(12) United States Patent
Shizukuishi

(10) Patent No.: US 9,808,159 B2
(45) Date of Patent: Nov. 7, 2017

(54) SOLID-STATE IMAGE SENSOR AND IMAGING APPARATUS INCLUDING THE SAME

(71) Applicant: Makoto Shizukuishi, Sendai (JP)

(72) Inventor: Makoto Shizukuishi, Sendai (JP)

(*) Notice: Subject to any disclaimer, the term of this patent is extended or adjusted under 35 U.S.C. 154(b) by 408 days.

(21) Appl. No.: 14/272,808

(22) Filed: May 8, 2014

(65) Prior Publication Data

US 2014/0334601 A1 Nov. 13, 2014

(30) Foreign Application Priority Data

May 8, 2013 (JP) .................................. 2013-098454

(51) Int. Cl.
*A61B 6/00* (2006.01)
*A61B 5/00* (2006.01)
*H01L 27/146* (2006.01)
*G01T 1/24* (2006.01)

(52) U.S. Cl.
CPC .......... *A61B 5/0062* (2013.01); *A61B 5/0035* (2013.01); *A61B 5/0077* (2013.01); *A61B 6/4233* (2013.01); *G01T 1/243* (2013.01); *H01L 27/14661* (2013.01); *H01L 27/14676* (2013.01); *A61B 6/4266* (2013.01); *H01L 27/14634* (2013.01)

(58) Field of Classification Search
CPC ......... H01L 27/14643; H01L 27/14661; H01L 27/14676
See application file for complete search history.

(56) References Cited

U.S. PATENT DOCUMENTS

| 4,810,881 | A | 3/1989 | Berger et al. |
| 5,315,101 | A | 5/1994 | Hughes et al. |
| 5,336,879 | A | 8/1994 | Sauer |
| 5,381,014 | A | 1/1995 | Jeromin et al. |
| 5,396,072 | A | 3/1995 | Schiebel et al. |
| 5,635,718 | A | 6/1997 | DePuydt et al. |
| 5,710,451 | A * | 1/1998 | Merchant ............ H01L 29/0847 257/140 |

(Continued)

FOREIGN PATENT DOCUMENTS

| JP | S6068767 A | 4/1985 |
| JP | S61-128565 A | 6/1986 |

(Continued)

*Primary Examiner* — Dani Fox
(74) *Attorney, Agent, or Firm* — Harness, Dickey & Pierce, P.L.C.

(57) ABSTRACT

An image sensor includes a first semiconductor chip including first and second surfaces; a second semiconductor chip including first and second surfaces; and a first adhesive layer between the second surface of the first semiconductor chip and the second surface of the second semiconductor chip, the first semiconductor chip being stacked on the second semiconductor chip via the first adhesive layer such that a footprint of the first semiconductor chip is larger than a footprint of the second semiconductor chip with respect to a plan view of the image sensor, the first semiconductor chip including an array of unit pixels configured to capture light corresponding to an image and to generate image signals based on the captured light, the second semiconductor chip including first peripheral circuits configured to control the array of unit pixels and receive the generated image signals.

18 Claims, 11 Drawing Sheets

(56) References Cited

U.S. PATENT DOCUMENTS

| | | |
|---|---|---|
| 6,552,319 B2 | 4/2003 | Pyyhtia et al. |
| 6,906,332 B2 | 6/2005 | Tashiro et al. |
| 7,355,642 B2 | 4/2008 | Suzuki et al. |
| 8,160,321 B2 | 4/2012 | Konishi |
| 8,536,670 B2 | 9/2013 | Yoshihara et al. |
| 8,659,148 B2 | 2/2014 | Tkaczyk et al. |
| 2003/0042425 A1 | 3/2003 | Tashiro et al. |
| 2005/0029643 A1 | 2/2005 | Koyanagi |
| 2006/0050160 A1* | 3/2006 | Suzuki ............. H01L 27/14634 348/294 |
| 2009/0046917 A1 | 2/2009 | Konishi |
| 2012/0056251 A1 | 3/2012 | Kudoh |
| 2012/0056288 A1 | 3/2012 | Yoshihara et al. |
| 2012/0120293 A1 | 5/2012 | Mabuchi |
| 2012/0133001 A1 | 5/2012 | Tkaczyk et al. |
| 2012/0147207 A1 | 6/2012 | Itonaga |
| 2013/0015328 A1 | 1/2013 | Goto |
| 2013/0033632 A1 | 2/2013 | Kishi |
| 2013/0092820 A1* | 4/2013 | Takemoto ............. H04N 5/369 250/208.1 |

FOREIGN PATENT DOCUMENTS

| | | |
|---|---|---|
| JP | S63-181369 A | 7/1988 |
| JP | H1093061 A | 4/1998 |
| JP | 2000-278605 A | 10/2000 |
| JP | 2001-291877 A | 10/2001 |
| JP | 2001-339057 A | 12/2001 |
| JP | 2002-090462 A | 3/2002 |
| JP | 2002-344809 A | 11/2002 |
| JP | 2003-078827 A | 3/2003 |
| JP | 2004-172228 A | 6/2004 |
| JP | 2007-044135 A | 2/2007 |
| JP | 2007-281690 A | 10/2007 |
| JP | 2009-049527 A | 3/2009 |
| JP | 2009-170448 A | 7/2009 |
| JP | 2011-228621 A | 11/2011 |
| JP | 2012-054450 A | 3/2012 |
| JP | 2012-104684 A | 5/2012 |
| JP | 2012-114189 A | 6/2012 |
| JP | 2012-118060 A | 6/2012 |
| JP | 5027339 B1 | 9/2012 |
| JP | 2012-199543 A | 10/2012 |
| JP | 2013-051674 A | 3/2013 |
| JP | 2013-080838 A | 5/2013 |
| JP | 2013-090127 A | 5/2013 |
| WO | WO-2006-112320 A1 | 10/2006 |
| WO | WO-2013-062052 A1 | 5/2013 |

\* cited by examiner

SOLID-STATE IMAGE SENSOR AND IMAGING APPARATUS INCLUDING THE SAME

CROSS-REFERENCE TO RELATED APPLICATION

This application claims priority under 35 U.S.C. §119 to Japanese Patent Application No. 2013-098454 filed on May 8, 2013, in the Japanese Patent Office (JPO), the entire contents of which are incorporated herein by reference.

BACKGROUND

1. Technical Field

Example embodiments relate to a large form factor solid state image sensor and an imaging apparatus using the same.

2. Related Art

Solid-state image sensors may be applied to medical instruments in order to enable the use of the medical instruments for discovering a disease or other condition harmful to the health of a patient in the early stages of the condition thereby reducing medical expenses. X-ray imaging systems may be used for this purpose.

Unlike a visible light image sensor, it may be difficult or, alternatively, impossible to use an optical lens system for refracting X-rays. Instead it may be desirable to use a large image size sensor or tiled image sensors including, for example, a so-called flat panel detector (FPD) which may have a size that is equal, or near equal, to that of the subject being photographed. Two types of large image size X-ray sensors have been developed. One of the types of X-ray sensors may include a photo-conductive material like amorphous selenium (a-Se) and thin film transistors (TFT) formed on a glass substrate. The other type of X-ray sensor may include an amorphous Si (a-Si) layer and thin film transistors (TFT) formed on a glass substrate. Further, a scintillator such as a cesium iodide (CsI) micro-crystalline layer may be applied on top of the a-Si layer to generate visible light emitted by incident X-ray. The X-ray image sensor using a photo-conductive material the same as or similar to a-Se is called a direct conversion type X-ray image sensor. The X-ray image sensor using a scintillator such as CsI micro-crystalline, on the other hand, is called an indirect conversion type X-ray image sensor. These conventional X-ray image sensors can be manufactured by the process technology similar to that of TFT used for a liquid crystal display (LCD). An LCD may include a liquid crystal layer and a TFT switching matrix formed on a glass substrate. An image size of the conventional X-ray image sensor may be 14 square inches, for example. However, it may be difficult for the conventional X-ray image sensors to capture a motion picture without image lag due to the large capacitive load and the TFT's slow switching speed. An angiocardiography, for example, may require a motion picture imaging to follow the actions of blood vessels around the beating heart.

A solid-state image sensor, for example a metal oxide semiconductor (MOS) sensor, has been applied to an X-ray imaging system to capture such a motion picture. The available image size of the MOS sensor, however, may be limited by the size of a silicon wafer used. A multifaceted FPD that combines plural MOS sensors, for example 4 sensors arranged in a 2×2 configuration, has been developed. Accordingly, available image sensing area of the FPD can be enlarged.

FIG. 1(a) shows a prior art of a MOS sensor. On the MOS sensor 1, a vertical scanning circuit 3, a horizontal scanning circuit 4, and a signal read-out circuit 5 are formed around a rectangular image sensing area 2. The signal read-out circuit 5 may include an analog to digital converter (ADC) and a co-related double sampling circuit (CDS) (not shown in this figure). A digital to analog converter (DAC) circuit 6, a timing pulse generation circuit 7, and a digital image processing circuit 8 are also included in the MOS sensor 1.

Input and/or output buffer circuits, input protection circuits, and an interface circuit (I/F) (not shown in this figure) may also be integrated on the periphery of the MOS sensor chip 1. These circuits and components discussed above as being included in portions of the MOS sensor chip other than the image sensing area 2 may be referred to as peripheral circuits.

The image sensing area 2 is formed by an array of unit pixels 13. The array includes m pixels horizontally by n pixels vertically to have m times n (i.e., m×n) pixels on the chip, for example, where 'm' and 'n' are both positive integers greater than 1. Each of the unit pixels 13 may include an optoelectronic conversion device including, for example, a pn-junction photo-diode and a MOS transistor circuit. A deep depletion layer, more than 50 micron meters in depth, for example, formed in the pn-junction of the unit pixels 13 may be necessary to improve the X-ray sensitivity because of the low absorption coefficient in Silicon (Si) with respect to the incident X-ray. A scintillator, for example, CsI micro-crystalline layer may be applied above the pn-junction to convert the incident X-ray to visible light, which may be effectively absorbed within 10 micron meters of depth in Si, for example. The MOS transistor circuit included in the unit pixels 13 may include a known three-transistor circuit composed of an amplifying transistor, a reset transistor, and a select transistor, for example. By controlling horizontal signal lines 10, charges stored in the photo-diode may be read out through the vertical signal line 11. The signal lines 10 may be connected to, and controlled by, the vertical scanning circuit 3. The signal lines 11 may be connected to the signal read-out circuit 5.

Another configuration of photo-diodes and the MOS transistor circuit is shown in FIG. 1(b). In the configuration illustrated by FIG. 1(b), every four pixels form a group. Each group may include a known MOS transistor circuit accompanying four photo-diodes 25-1, 25-2, 25-3, and 25-4. The MOS transistors 18-1, 18-2, 18-3 and 18-4 may be switched by the read control signals 10-1, 10-2, 10-3 and 10-4. Photo-generated charges stored in each photodiode may be transferred to the gate electrode of the MOS transistor 18-6, and reset by the MOS transistor 18-5. Consequently, the number of the MOS transistors per pixel may be 1.5 transistors, and the number of the global lines per pixel in the horizontal direction may be 1.25 lines per pixel. Two types of wiring are defined. One type of wiring is local wiring which runs inside the pixel. The other type of wiring is global wiring which runs over multiple pixels or across the image sensing area 2. Examples of global wiring include lines 10 and 11 in FIG. 1(a), and lines 10-1, 10-2, 10-3, 10-4 and 11 in FIG. 1(b).

As shown in FIG. 1(c), the signal read-out circuit 5 may include comparators 14-1 and counters 14-2 to form a series of ADCs in a column direction. Image signals transferred by the global wiring 11 may be compared with the output signal of the DAC 6. Digitized signals may be outputted by controlling the signal lines 12. As shown in FIG. 1(d), the vertical scanning circuit 3 and the horizontal scanning circuit 4 may include flip-flop circuits 15 and logic gates 16 to form shift registers in row and column directions respectively. Having control (Con.), start (Sta.) and clock (Clk.)

signals, output signal pulses 10 and 12 with predetermined timings and pulse widths may be generated to control the vertical scanning circuit 3 and the horizontal scanning circuit 4, which are arranged in a row and column direction, respectively, so as to be aligned with the arrangement of pixels in horizontal and vertical directions. For example, though the scanning circuit in FIG. 1(d) is illustrated as being arranged in the row direction as an example of the vertical scanning circuit 3, the scanning circuit in FIG. 1(d) may also be arranged in the column direction as an example of the horizontal scanning circuit 4. Photo-conductive materials including, for example a-Se or a-Si, may be deposited with a scintillator on the top of the MOS sensor to generate photo-excited charges effectively when exposed to an incident beam of high energy light including, for example, an X-ray beam.

In the example illustrated in FIG. 1(a), peripheral circuits including the vertical scanning circuit 3, the horizontal scanning circuit 4 and the signal read-out circuit 5 are located next to vertical and horizontal sides of the image sensing area 2. These peripheral circuits located by the image sensing area 2 on the chip are examples of dead space. The term dead space refers to areas of the MOS image sensor 1 that are light-insensitive. As used herein, the term image sensing area refers to an array of unit pixels. Isolation areas in between light-sensitive elements of unit pixels are not light-sensitive. However, though isolation areas in between pixels of the image sensing area 2 are not light sensitive, as used herein, the term dead space refers to peripheral circuits and I/O components including an input protector outside of the image sensing area, and the term dead space does not refer to an isolation area between the pixels of the image sensing area. Examples of peripheral circuits that are dead space include the vertical scanning circuit 3, the horizontal scanning circuit 4, the signal read-out circuit 5 and other peripheral circuits including a DAC 6, a timing pulse generation circuit 7, a digital image processing circuit 8, an interface circuit, input and/or output buffer circuits, input protection circuits, and contact pads 9.

As the size of the MOS sensor is increased, the image sensing area may become dominant over the peripheral circuits because the area for the input and/or output buffer circuits, input protection circuits and contact pads are not necessarily proportional to the area for the image sensing area. Consequently, if a surface area of an image sensor is increased by a certain percentage and a number of pixels in the image sensor is increased, a surface area of an image sensing portion of the chip may become larger by an even greater percentage.

Stacked or three dimensional (3D) sensor structures have been developed to enlarge the image sensing area on a first chip, which is stacked on the second chip. The horizontal scanning circuits and vertical scanning circuit that are composed of a series of unit circuits including, for example, a shift register circuit, may be arranged in a row and column direction so as to be aligned with the arrangement of pixels in horizontal and vertical directions respectively. In the stacked type sensor, however, peripheral circuits like the horizontal and the vertical scanning circuits may be integrated on the second semiconductor chip. Further, control signal lines to, and output signal lines from, each pixel should be routed between the first and the second semiconductor chips.

As is mentioned above, the vertical and horizontal scanning circuit 3 and 4 may have a series of shift registers which correspond to each line of the horizontal and vertical global wiring 10 and 11, respectively. Straight and same pitch global lines may be routed with the pixel array and such routing may suppress fixed pattern noise due to signal delay non-uniformity. With respect to the conventional stacked structure, the first semiconductor chip should be stacked on the larger size of the second semiconductor chip in order to keep the above-mentioned same routing pitch of the global lines or shift register layout pattern. The second semiconductor chip, in such a case, may have a large blank or unused area unless the second semiconductor chip is hooked or L-shaped. However, a hooked or L-shaped semiconductor chip may be difficult for a wafer dicing machine to cut or form.

It should be also noted that the semiconductor chip may be damaged by high energy particles or radiation like X-ray beam. As for the MOS image sensor, charges trapped in silicon dioxide ($SiO_2$) may cause a shift in threshold voltages of MOS transistors of the MOS image sensor. This shift in threshold voltages may cause image quality of the MOS image sensor to deteriorate and eventually reduce a product life time of the MOS image sensor.

SUMMARY

Example embodiments provide a MOS sensor and an X-ray system including the same. Example embodiments provide a MOS sensor that has a relatively large image sensing area and is capable of motion picture imaging with relatively low image lag. In addition, example embodiments further provide a MOS sensor that includes little or no dead space on the sensor surface. Example embodiments still further provide a MOS sensor having a curved surface. In addition, example embodiments provide a MOS sensor that is capable of preventing or limiting radiation damage.

According to example embodiments, an image sensor may include a first semiconductor chip having a first surface and a second surface, the first semiconductor chip including an array of unit pixels configured to capture one or more incident beams of light (i.e., electromagnetic radiation) including, for example X-rays, or light corresponding to an image, and configured to generate image signals based on the captured one or more incident beams, the array of unit pixels forming a light sensitive area on the first surface of the first semiconductor chip; and a second semiconductor chip having a first surface and a second surface, the second semiconductor chip including first peripheral circuits configured to control the array of pixels and receive the generated image signals, the first peripheral circuits including a vertical scanning circuit, a horizontal scanning circuit, and a signal read-out circuit, the first semiconductor chip being stacked on the second semiconductor chip such that the second surface of the first semiconductor chip faces the second surface of the second semiconductor chip, the first semiconductor chip being larger than the second semiconductor chip.

Example embodiments provide a MOS sensor having stacked structure of two semiconductor chips. The MOS sensor may include an image sensing area as a detector of two dimensional image information formed on a first surface of a first semiconductor chip of the two stacked semiconductor chips, and pixel circuits connecting with global wiring may be formed on a second surface of the first semiconductor chip. According to example embodiments, the image sensing area may include only unit pixels, and the first semiconductor chip may be formed such that the first surface of first semiconductor chip includes only the image sensing area, and no peripheral circuits. A vertical scanning circuit, a horizontal scanning circuit, a signal read-out circuit and other peripheral circuits may be formed on a second surface of the second semiconductor chip of the two stacked semiconductor chips. Further, external input and output terminals, which are electrically connected with the circuits formed on a second surface of the second semiconductor chip by a through silicon via (TSV), may be formed on a first surface of the second semiconductor chip. The two stacked semiconductor chips of the MOS sensor may be stacked such that the second surfaces of the first and second semiconductor chips face each other. Further, the MOS sensor may include electrical contacts between the stacked two semiconductor chips. Further, according to example embodiments, in a plan perspective view, the vertical scanning circuit, the horizontal scanning circuit, the signal read-out circuit and other peripheral circuits are located on a portion of the second surface of the second semiconductor chip that falls inside a footprint of the image sensing area formed on the first surface of the first semiconductor chip above the second semiconductor chip, for example with respect to a plan view of the MOS sensor. In the configuration described above, the dead space may be reduced, and the image sensing area can be increased on the first surface of the first semiconductor chip. Further, the increased image sensing area may allow for increased pixel size of the unit pixels. Due to increased pixel size, a MOS image sensor according to example embodiments may have increased sensitivity when compared with a conventional MOS image sensor having the same chip size and total number of pixels as the MOS image sensor according to example embodiments.

According to example embodiments, a silicon substrate of the first semiconductor chip may have a thickness in a range of 0.5 to 20 microns. With such a configuration, a MOS image sensor according to example embodiments may be bent easily with less or relatively low mechanical stress.

According to example embodiments, a type of the MOS transistors in the MOS transistor circuit formed in the first semiconductor chip either PMOS or NMOS (i.e., not both PMOS and NMOS type transistors), and a type of the MOS transistors in the MOS transistor circuit formed in the second semiconductor chip is CMOS (i.e., both PMOS and CMOS type transistors). With such a configuration, the temperatures used in the manufacturing process of the first semiconductor chip and an amount of time dedicated to impurity diffusion the manufacturing process of the first semiconductor chip may both be reduced thereby preventing warping of the silicon wafer before stacking the first semiconductor chip on the second semiconductor chip.

Moreover, according to example embodiments, several or all of the peripheral circuits may be shaped as rectangles having two parallel long sides and two parallel short sides, and the peripheral circuits may be arranged on the second surface of the second semiconductor chip such that a long side of the vertical scanning circuit block is parallel to a long side of the horizontal scanning circuit block. Further, external input and output terminals may be formed on the first surface of the second semiconductor chip. Due to the manner in which the external input and output terminals are formed on the second semiconductor chip, a size of the second semiconductor chip may be relatively small, and it may not be necessary to form the second semiconductor chip in a hooked shape or an L-shape to reduce the size of the second semiconductor chip. Instead, according to example embodiments, the second semiconductor chip may be formed in a rectangular shape, which may make result in lower manufacturing costs for the second semiconductor chip and the MOS image sensor.

According to example embodiments, in a plan perspective view, each line included in first global wiring may intersect at, for example, right angles with each line included in second global wiring. Each line included in the second global wiring may be electrically connected to each line included third global wiring at, for example, right angles. As a result, each line of the first global wiring may be, for example, parallel to each line of the third global wiring. In other words, the second global wiring may change direction from 90 degree to become, for example, parallel to the first wiring group. The first wiring may be a set of horizontal global lines and the second global wiring may be a set of vertical global lines and vice versa. Though right-angle and parallel arrangements of global wiring are discussed above as examples, example embodiments are not limited to parallel or right angle arrangements, and other angles may be used to arrange the global wiring.

According to example embodiments, the first and second semiconductor chips may have the shapes of rectangles and may each have two parallel longer sides and two parallel shorter sides. Further, the lengths of the shorter sides of the first semiconductor chip may be substantially the same or the same as the lengths of the longer sides of the second semiconductor chip when the first semiconductor chip is stacked on the second semiconductor chip such that the longer sides of the first semiconductor chip are perpendicular to the longer sides of the second semiconductor chip. Further, the lengths of the longer sides of the first semiconductor chip may be substantially the same or the same as the lengths of the longer sides of the second semiconductor chip when the first semiconductor chip is stacked on the second semiconductor chip such that the longer sides of the first semiconductor chip are parallel to the longer sides of the second semiconductor chip. With such a configuration, for a MOS image sensor according to example embodiments, the distance or pitch between the lines of the global wiring associated with the pixel signal outputs may be same as that of ADCs in the signal read-out circuit.

According to example embodiments, the first global wiring may be directly connected to the signal read-out circuit at right angle with respect to the longer sides of the read out circuit. With such a configuration, it may not be necessary to extend signal lines of the first global wiring with respect to one another in order to connect with the signal read-out circuit, and thus, the electrical load of each signal line may be kept uniform.

According to example embodiments, with respect to a plan perspective view, the signal read-out circuit may be located in the middle region of the image sensing area. For example, when the image sensing area is rectangular, the center of the signal read-out circuit may be located substantially equidistant or equidistant from the four sides of the image sensing area. With such a configuration, the input terminals on the signal read-out circuit may be connected to the centers of each of a plurality of lines of global wiring that are formed on the second surface of the first semiconductor chip and run perpendicular to the longer sides of the signal read-out circuit. Such a configuration may result in lower image shading observed in the re-produced image because of the reduction in line load difference, in comparison with another example configuration where input terminals are placed near the ends of the signal lines and/or lines of global wiring.

According to example embodiments, the first semiconductor chip may be stacked on a series of the second semiconductor chips such that the longer sides of each of the second semiconductor chips are parallel to the longer sides of the first semiconductor chip. With such a configuration, the lengths of the longer sides for each of the series of second semiconductor chips may be reduced relative to the configuration where the first semiconductor chip is stacked on only one second semiconductor chip. This arrangement may facilitate the chip handling and mounting process and may result in a higher production yield.

According to example embodiments, an interposer may be stacked between the first and the second semiconductor chips. With such a configuration, the miniaturized TSV and multi-layered wiring structure formed in the interposer may result in simplification of signal traffic and a wiring layout between the first and second semiconductor chips.

According to example embodiments, a semiconductor chip; on which a digital signal processing circuit (DSP) and a data compression circuit are integrated, may be stacked on the interposer. With such a configuration, digital data transferred from the signal read-out circuit may be compressed before outputting the image data and, as a result, the data transfer rate may be increased without increasing the clock frequency.

According to example embodiments, an array of pixel electrodes may be formed on the first surface of the first semiconductor chip. A photo-conductive material or layer may be applied on top of the pixel electrodes. A counter electrode may be deposited on the photo-conductive material or layer. Each pixel electrode may be electrically connected with each pixel output terminal on the second surface of the first semiconductor chip by TSVs. With such a configuration, a large photo-conductive area may be formed with relative ease by physical or chemical vapor deposition of a photo-conductive material or layer.

According to example embodiments, a direct conversion type photo-conductive material may be applied on top of the MOS sensor. Further, the direct conversion type photo-conductive material may include amorphous and micro-crystalline semiconductors, and other organic and/or inorganic photo-conductive compounds, for example. With such a configuration, various energy or wave length incident beam may be detected using desirable materials. In addition, the image sensing area may be enlarged with relative ease without overlaying a scintillator.

According to example embodiments, a silicon substrate of the second semiconductor chip may have a thickness in a range of 50 nanometers to 1 micron meter. With such a configuration, a MOS image sensor according to example embodiments may have lower risk of radiation damage being caused in the second semiconductor chip.

According to example embodiments, a flat panel detector (FPD) formed by tiled multiple MOS sensors is disclosed. With such a configuration, an entire image sensing area may be enlarged, and as a result, one or both of parallel data read-out and higher data transfer rate may be realized without increasing a clock frequency or power consumption.

According to example embodiments, a photo-conductive material or layer is applied on top of more than one of the first semiconductor chips. Pixel electrodes are placed on the first semiconductor chips uniformly such that, for each of the first semiconductor chips, the electrodes have the same distance or pitch between them. With such a configuration, an available image sensing area may be enlarged with relative ease by physical or chemical vapor deposition of the direct conversion materials. In addition, a dead space on the entire image sensing area may be reduced, minimized or removed, and equal pixel sampling points may be kept on each MOS sensor and between the MOS sensors.

According to example embodiments, an X-ray imaging system using a FPD in accordance with example embodiments is disclosed. With such a configuration, an available image sensing area of the X-ray imaging system may be enlarged due to the inclusion of include little or no dead space. Further, the X-ray imaging system may be used to and used to capture images with a higher data transfer rate which facilitates a motion picture capturing.

According to example embodiments, a FPD in accordance with example embodiments is disclosed. With such a configuration, incident beams of light, (i.e., electromagnetic radiation) including, for example, X-rays that pass through an object may be received at the sensor surface at right angles to realize uniform sensitivity and magnification over the image sensing area.

According to example embodiments, an X-ray imaging system using a FPD having a curved surface in accordance with example embodiments is disclosed. With such a configuration, an isotropic 3D volume data may be obtained by computer tomographic (CT) scanning with a lower X-ray dose and shorter examination time relative to non-curved FPDs.

BRIEF DESCRIPTION OF THE DRAWINGS

The above and other features and advantages of example embodiments of the inventive concepts will become more apparent by describing in detail example embodiments of the inventive concepts with reference to the attached drawings. The accompanying drawings are intended to depict example embodiments of the inventive concepts and should not be interpreted to limit the intended scope of the claims. The accompanying drawings are not to be considered as drawn to scale unless explicitly noted.

DETAILED DESCRIPTION OF EXAMPLE EMBODIMENTS

Figure 1A:
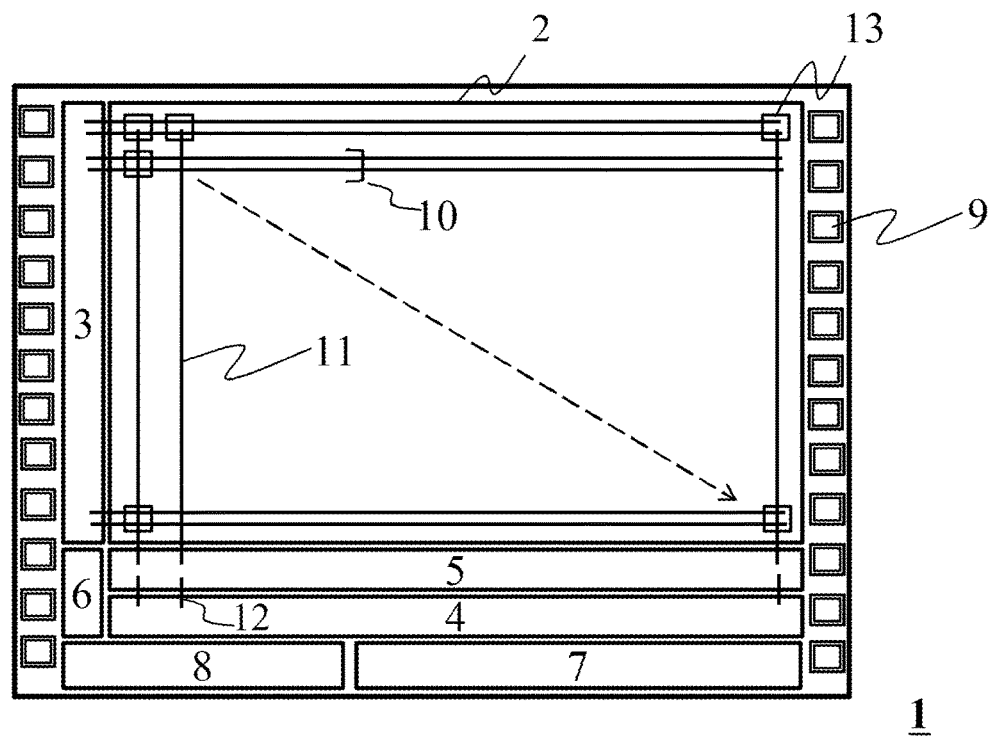
FIG. 1(a) is a diagram illustrating a plan view of a conventional MOS sensor.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected to", "coupled to", or "on" another element, it may be directly connected to, directly coupled to, or directly on the other element, or intervening elements may be present. In contrast, when an element is referred to as being "directly connected to", "directly coupled to", or "directly on" another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As is discussed above, X-ray imaging systems may be used with medical instruments in order to enable the discovery of a disease or other condition harmful to the health of a patient in the early stages of the condition thereby reducing medical expenses. Further, for the above-referenced applications of an X-ray imaging system, other functionalities, a larger image size, a higher data transfer rate with lower power consumption, and lower chip radiation damage besides sensitivity and image quality should be considered. For example, it may be desirable for an X-ray imaging system to provide high speed image recognition in order to enable motion picture imaging for active or moving photographic subjects.

Further, as is discussed above, an available image sensing area of an FPD may be enlarged by combining, for example 4 MOS sensors arranged in a 2×2 configuration. However, it may be desirable to reduce, minimize or remove a light insensitive area either on the image sensing areas of the individual MOS sensors or between the MOS sensors, in order to enable the use of a dead space free image sensor for capturing a higher quality image.

Figure 2A:
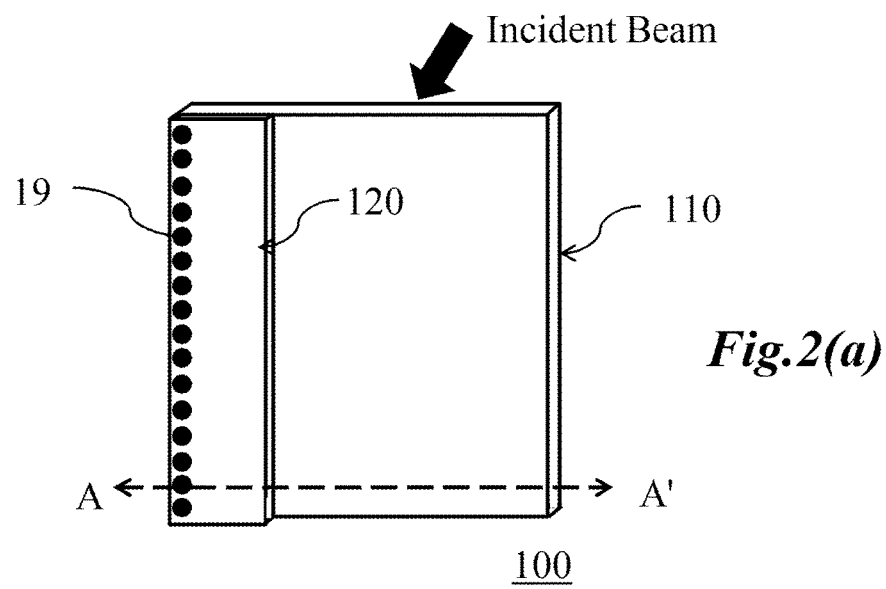
FIG. 2(a) is a diagram illustrating a perspective view of a MOS sensor according to at least one example embodiment.

With reference to the accompanying drawings, a MOS sensor having for example, little or, alternatively, no dead space on its top surface according to at least one example embodiment is described below. FIG. 2(a) is a diagram illustrating a perspective view of the bottom of a MOS sensor 100, which includes a first semiconductor chip 110 stacked on a second semiconductor chip 120. The first semiconductor chip 110 has an image sensing area 2 (which is not shown in this figure) on the first surface of the first semiconductor chip 110. The image sensing area 2 is defined by the unit pixels 13 on the first surface of the first semiconductor chip 110. An array of pixel read-out circuits may be formed on the second surface of the first semiconductor chip 110, where the second surface of the first semiconductor chip 110 is opposite to the first surface of the semiconductor chip 110. The pixel read-out circuits may convert beams of light (i.e., electromagnetic radiation) incident on the image sensing area 2 on the first surface of the first semiconductor chip 110 into electrical signals. For example, FIG. 2(a) includes an arrow illustrating a direction of a beam of light that is incident on the image sensing area 2 located on the first surface of the first semiconductor chip 110, which is opposite to the second surface of the first semiconductor chip 120. External input and output terminals 19 may be formed on the bottom of the MOS sensor on a first surface of the second semiconductor chip 120. The first semiconductor chip 110 is stacked on the second semiconductor chip 120, where the second surface of the first semiconductor chip 110 faces the second surface of the second semiconductor chip 120. Further, the first semiconductor chip 110 may be larger than the second semiconductor chip 120. For example, with respect to a plan view of an MOS sensor according to example embodiments, a foot print of the first semiconductor chip 110 may be larger than a foot print of the second semiconductor chip 120 upon which the first semiconductor chip 110 is stacked. According to example embodiments, a size of the image sensing area 2 of the first semiconductor chip 110 may be, for example, up to 1 sq. in., 1 sq. in., between 1 sq. in. and the size of a business card (e.g. 7 sq. in.), 7 sq. in., or larger than 7 sq. in. If, as in some conventional image sensors, the second semiconductor chip 120 was larger than the first 110 having an image sensing area 2 of the example sizes discussed above, a large portion of the second semiconductor chip 120 (e.g., 80%) may be unused or vacant. Forming the second semiconductor chip 120 in such a manner may be costly. Accordingly, as is discussed above, according to example embodiments, the size of the second semiconductor chip 120 is smaller than the size of the first semiconductor chip 110, and thus, an amount of the costly unused or vacant area on the second semiconductor chip 120 may be reduced or, alternatively minimized. According to example embodiments, peripheral circuits (not shown in FIG. 2(a)) including one or more of a vertical scanning circuit, a horizontal scanning circuit, a signal read-out circuit (including, for example, an analog-to-digital converter (ADC)), a digital-to-analog converter (DAC), a timing pulse generation circuit, a digital image processing circuit, an interface circuit, input and/or output buffer circuits, input protection circuits, and contact pads (which is not shown in this figure) may be formed on the second surface of the second semiconductor chip 120, and are not formed on the first surface of the first chip 110. For example, according to example embodiments, the image sensing area 2 may include only unit pixels 13, and the first semiconductor chip 110 may be formed such that the first surface of first semiconductor chip includes only the image sensing area, and no peripheral circuits. With this configuration, the image sensing area 2 on the first surface of the first semiconductor chip 110 may be enlarged without increasing the area for the peripheral circuit around the image sensing area, and the size of the second semiconductor chip 120 may be reduced or, alternatively, minimized.

As is discussed in greater detail below, peripheral circuits, and external input and output terminals may be located at a position on the second surface of the second semiconductor chip that is below the image sensing area 2 of the first semiconductor chip. For example, the peripheral circuits, and external input and output terminals may be located on a portion of the second surface of the second semiconductor chip that falls within a footprint of the image sensing area 2 formed on the first surface of the first semiconductor chip above the second semiconductor chip, for example with respect to a plan view of the MOS sensor.

According to example embodiments, the first semiconductor chip 110 may be formed to include only the image sensing area 2, or, alternatively, the first semiconductor chip 110 may be formed to include only the image sensing area 2 and a dicing or scribe margin surrounding the image sensing area 2. Further, the image sensing area 2 may be formed to include only unit pixels 13 and the isolation area that separates the unit pixels 13 such that the image sensing area 2 includes none of the peripheral circuits. According to example embodiments, the first semiconductor chip 110 may be formed to include none of the peripheral circuits.

Figure 2B:
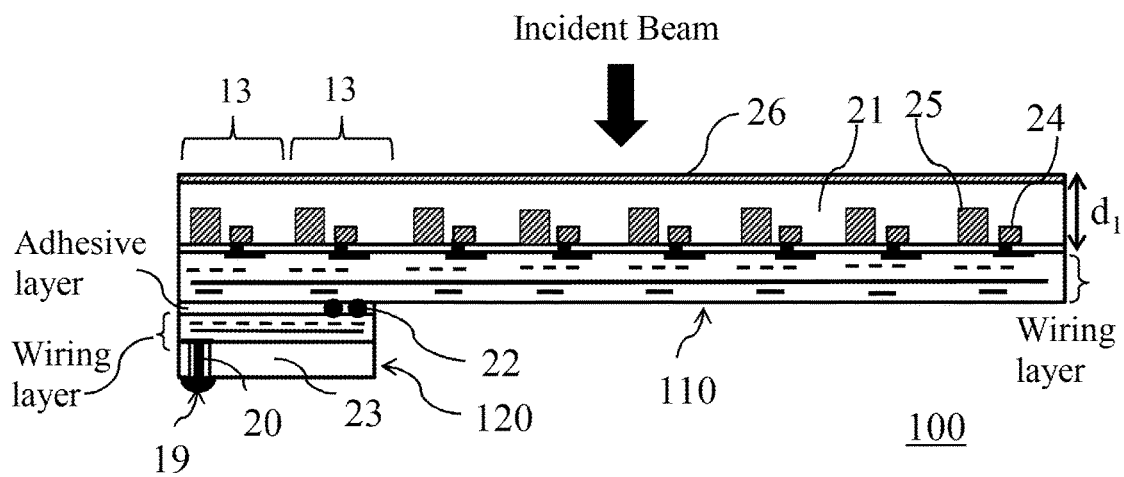
FIG. 2(b) is a diagram illustrating a cross sectional view taken along line A-A' of the MOS sensor illustrated in FIG. 2(a) according to at least one example embodiment.

FIG. 2(b) is a diagram illustrating a cross sectional view taken along line A-A' of the MOS sensor 100 illustrated in FIG. 2(a) according to at least one example embodiment. In the example illustrated in FIG. 2(b), the first semiconductor chip 110 is stacked on the second semiconductor chip 120, for example, with the use of an insulating adhesive layer. High impurity concentration n-type region ($n^+$) 25 is embedded in a p-type silicon substrate 21 to form a pn photo-diode in each pixel 13. In the example illustrated in FIG. 2(b), a high impurity concentration thin p-type region ($p^+$) 26 is formed on the first surface of the first semiconductor chip 110. MOS transistor circuits are formed on the silicon substrate 21 opposite to the first surface of the first semiconductor chip 110. MOS transistor circuits may include an impurity doped diffusion area 24 to serve as a source and drain region.

According to example embodiments, it may be desirable for the MOS transistor circuit type formed in the first semiconductor chip 110 to be only one of a PMOS or an NMOS type, not a CMOS type circuit that includes both PMOS and NMOS transistors. For example, it may be desirable for the MOS transistor circuit type formed in the first semiconductor chip 110 to be NMOS only. In the case of an n-type silicon substrate 21, on the other hand, high impurity concentration p-type region ($p^+$) 25 may be embedded to form a pn photo-diode in each pixel 13. A high impurity concentration thin n-type region ($n^+$) 26 may be formed on the first surface of the first semiconductor chip 110.

Further, according to example embodiments, it may be preferable for the MOS transistor circuit type formed in the second semiconductor chip to be a CMOS type. With such a configuration, latch-up (a CMOS-related short circuit failure) may be prevented in the first semiconductor chip. In addition, the manufacturing process of the first semiconductor chip may be completed, for example, without applying a high temperature or using a lengthy impurity diffusion period to form a deep p-well and/or n-well, and thus, the occurrence of thermal strain and a warping of the silicon wafer before stacking the second semiconductor chip on the first semiconductor chip may be avoided.

According to example embodiments, the thickness ($d_1$) of the silicon substrate 21 of the first semiconductor chip 110 may have a range of, for example, 0.5 to 20 micron meters. With such a configuration, a MOS image sensor according to example embodiments may be bent more easily with less mechanical stress.

In the example illustrated in FIG. 2(b), external input and output terminals 19 are formed on the first surface of the second semiconductor chip 120. The external input and output terminals 19 may be electrically connected to the electrical pads on the second surface of the second semiconductor chip 120 by through silicon vias (TSV)s 20. Each input terminal may have an input protection circuit (which is not shown in this figure) on the second surface of the second semiconductor chip 120. The electrical pads on the second surface of the second semiconductor chip 120 may be electrically connected to the electrical pads on the second surface of the first semiconductor chip 110 by micro-bumps 22. Further, with respect to the above referenced conventional image sensor using a glass substrate, the second semiconductor chip may not be stacked on the back side of the glass substrate, but rather the second semiconductor chip may be stacked on the photo-conductive material or layer or TFT side because it may be difficult to form electrical contacting means such as the TSV in the glass substrate, which may be more than 1 millimeter in thick. According to example embodiments, the first and second semiconductor chips 110 and 120 may both be shaped as rectangles where the size of a footprint of the second semiconductor chip 120 is smaller than that of the first semiconductor chip 110 with respect to, for example, a plan view of the MOS sensor 100 according to example embodiments. For example, according to example embodiments, the MOS sensor 100 may be configured such that none of the boundaries of a footprint of the second semiconductor chip 120 fall outside the boundaries of a footprint of the first semiconductor chip 110. For example, according to example embodiments, a footprint of the first semiconductor chip 110 may overlap a footprint of the second semiconductor chip 120 entirely, with respect to a plan view of the MOS sensor 100. Further, according to example embodiments, peripheral circuits, and external input and output terminals may be located on a portion of the second surface of the second semiconductor chip 120 that falls within a footprint of the image sensing area 2 formed on the first surface of the first semiconductor chip 110 above the second semiconductor chip 120, for example with respect to a plan view of the MOS sensor 100. Examples of peripheral circuits included in the second semiconductor chip 120 are discussed in greater detail below with reference to FIG. 3(b).

Figure 1B:
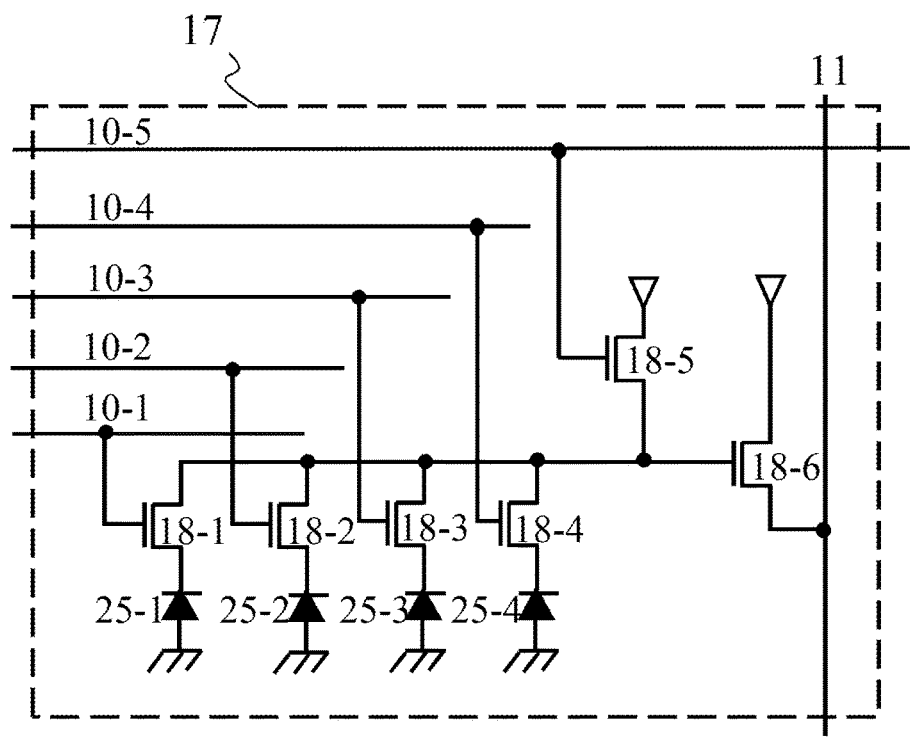
FIG. 1(b) is a diagram illustrating a plan view of a conventional four pixel structure with a common source follower amplifier circuit.
Figure 1C:
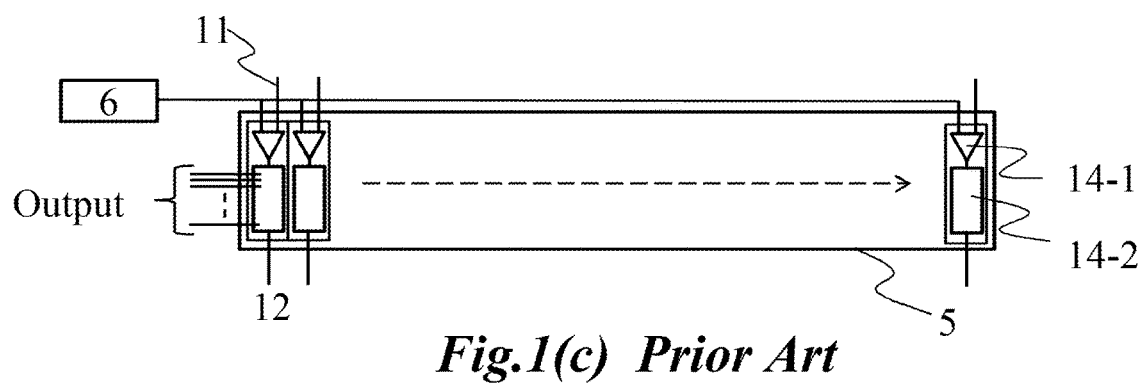
FIG. 1(c) is a diagram illustrating a plan view of a signal read-out circuit.
Figure 3A:
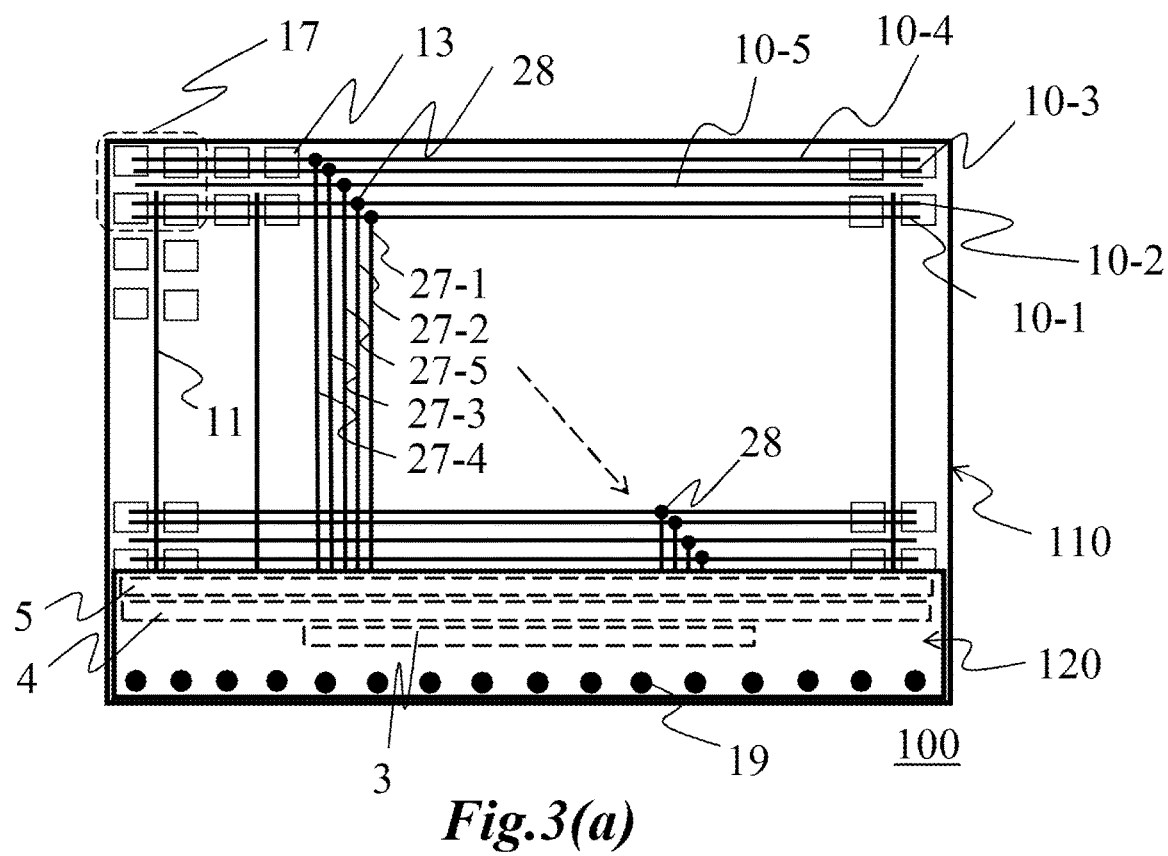
FIG. 3(a) is a diagram illustrating an example a layout of global wiring of first and second semiconductor chips of a MOS sensor according to at least one example embodiment, with respect to a plan view of a bottom side of the MOS sensor.
Figure 3B:
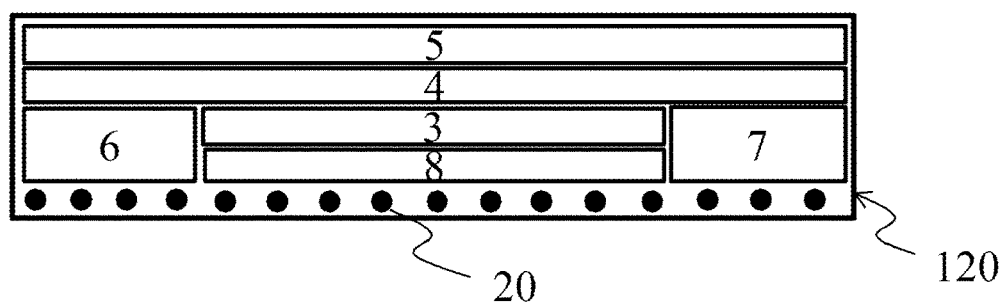
FIG. 3(b) is a diagram illustrating an example of circuit block layout on a second semiconductor chip according to at least one example embodiment, with respect to a plan view of the second semiconductor chip.

FIG. 3(a) is a diagram illustrating an example a layout of global wiring of first and second semiconductor chips 110 and 120 of the MOS sensor 100 according to at least one example embodiment, with respect to a plan view of a bottom side of the MOS sensor. FIG. 3(b) is a diagram illustrating an example of circuit block layout on a second semiconductor chip according to at least one example embodiment, with respect to a plan view of the second semiconductor chip. FIG. 3(a) and FIG. 3(b) show a plan view of the second surface of the first semiconductor chip 110 and a plan view of the second surface of the second semiconductor chip 120, respectively according to example embodiments. As is illustrated n FIG. 3(b), examples of peripheral circuits that are included in the second semiconductor chip 120 include the vertical scanning circuit 3, the horizontal scanning circuit 4, the signal read-out circuit 5 and other peripheral circuits including a DAC 6, a timing pulse generation circuit 7, and a digital image processing circuit 8. In FIG. 3(a), every four pixels form a pixel group 17, as is indicated by dotted line illustrated around a pixel group 17 in FIG. 3(a). Each pixel group includes a MOS transistor circuit having a known structure for handling four photo-diodes as shown in FIG. 1(b). The charges stored in the four photo-diodes may be switched by the read control signals 10-1, 10-2, 10-3 and 10-4. The charges stored in the four photo-diodes may be switched by the read control signals 10-1, 10-2, 10-3 and 10-4. Three rectangles illustrated by dashed lines within the second semiconductor chip 120 in FIG. 3(a) indicate the positions of the vertical scanning circuit 3, the horizontal scanning circuit 4 and the signal read-out circuit 5 on the second surface of the second semiconductor chip 120. In the example illustrated in FIG. 3(b), the vertical scanning circuit 3 is rotated 90 degrees such that a long side of the rectangular vertical scanning circuit 3 becomes, for example, parallel to a long side of the rectangular horizontal scanning circuit 4, where the vertical scanning circuit 3 and the rectangular horizontal scanning circuit 4 each have a pair of parallel longer sides and a pair of parallel shorter sides as illustrated in FIG. 3(b). With such a configuration, the second semiconductor chip 120 may have, for example, a flat rectangular shape, and it may not be necessary for the second semiconductor chip 120 to be hooked or L-shaped. Accordingly, the second semiconductor chip 120 may be smaller in size and the cost of manufacturing the second semiconductor chip 120 may be lower. Moreover, forming the second semiconductor chip with a narrow or thin rectangular shape may facilitate the stacking of the first semiconductor chip 110 on the second semiconductor chip 120, for example when the first semiconductor chip 110 has a curved or bent shape.

In the example illustrated in FIGS. 3(a) and 3(b), lines of the signal global wiring 11 are directly connected to the micro-pads (which are not shown in this figure) on the signal read-out circuit 5. Further, according to example embodiments, lines of the global wiring associated with pixel control signals may be arranged parallel to the lines of the global wiring 11. The read select global wiring lines 10-1, 10-2, 10-3, 10-4, and reset global wiring line 10-5 are connected to the micro-pads on the vertical scanning circuit 3 through read select global wiring lines 27-1, 27-2, 27-3, 27-4, and reset global wiring line 27-5, respectively. According to example embodiments, the read select global wiring lines 10-1, 10-2, 10-3, 10-4, and reset global wiring lines 10-5 may meet the read select global wiring lines 27-1, 27-2, 27-3, 27-4, and the reset global wiring 27-5 line at contact points 28 at, for example, right angles. Further, the read select global wiring lines 27-1, 27-2, 27-3, 27-4, and the reset global wiring line 27-5 may be, for example, parallel to the global wiring lines 11. According to example embodiments, because they do not cross each other, the read select global wiring lines 27-1, 27-2, 27-3, 27-4, and the reset global wiring line 27-5 may be formed by the same metal layer as the global wiring line 11. With such a configuration, the length in longitudinal direction of the vertical scanning circuit 3 can be maintained without size reduction, and all wiring lengths or load capacitance of the global wiring 11 may be uniform. Though only one example pixel group 17 is highlighted in FIG. 3(a) using a dashed box for the purpose of simplicity, all unit pixels 13 in the first semiconductor chip 110 may be included in a corresponding pixel group 17 of, for example, four unit pixels 13. Further, though FIG. 3(a) focuses on global wiring lines corresponding to the example pixel group 17 indicated in FIG. 3(a), all pixel groups 17 may be connected to global wiring lines in the same manner described above with respect to the example pixel group 17.

Figure 4A:
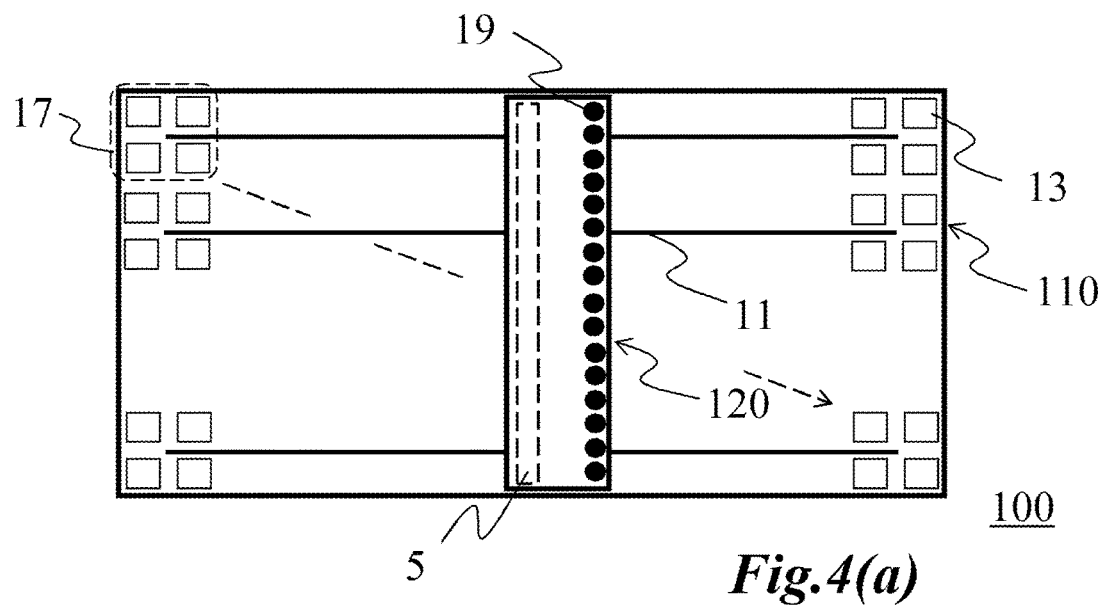
FIG. 4(a) is a diagram illustrating an example location of a second semiconductor chip relative to a first semiconductor chip according to at least one example embodiment, with respect to a plan view of a bottom side of the MOS sensor.
Figure 4B:
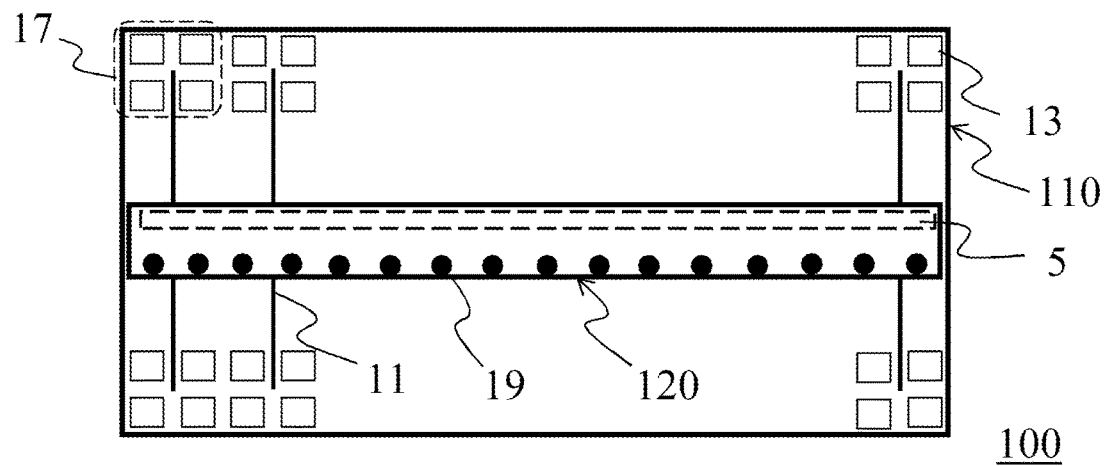
FIG. 4(b) is a diagram illustrating an example location of a second semiconductor chip relative to a first semiconductor chip according to at least one example embodiment, with respect to a plan view of a bottom side of the MOS sensor.

FIGS. 4(a) and 4(b) are diagrams illustrating different example locations of the second semiconductor chip 120 relative to the first semiconductor chip 110 according to at least one example embodiment, with respect to a plan view of a bottom side of the MOS sensor 100. FIGS. 4(a) and 4(b) show plan views of the second surface of the first semiconductor chip 110 and the first surface of the second semiconductor chip 120 for configurations of the MOS sensor 100 in which the first semiconductor chip 110 and the second semiconductor chip 120 are stacked such that the second semiconductor chip 120 is stacked below a central portion of the first semiconductor chip 110, according to example embodiments. In the example illustrated in FIGS. 4(a) and 4(b), lines of the global wiring 11 are electrically connected to the micro-pads (which are not shown in FIGS. 4(a) and 4(b)) on the signal read-out circuit 5 on the second surface of the second semiconductor chip 120. Further, according to example embodiments, lines of the global wiring associated with pixel control signals (which are not shown in FIGS. 4(a) and 4(b)) may be arranged parallel to the lines of the global wiring 11, in a manner similar to that discussed above with reference to FIG. 3(a).

Similar to the configuration of the MOS sensor 100 illustrated in FIG. 3(a), in the MOS image sensor 100 illustrated in FIGS. 4(a) and 4(b), lines of the third global wiring (e.g., lines corresponding to global wiring lines 10-1-10-5 illustrated in FIG. 3(a)) may be formed to connect with lines of the second global wiring (e.g., lines corresponding to global wiring lines 27-1-27-5 illustrated in FIG. 3(a)) which are connected to either a horizontal or a vertical scanning circuit included, for example, on the second surface of the second semiconductor chip 120. According to example embodiments, the first global wiring 11 may be directly connected to the signal read-out circuit 5 at right angle, for example, with respect to the longer parallel sides of the rectangular read-out circuit 5. With such a configuration, it may not be necessary for signal lines of the first global wiring 11 to be extended with respect to one another in order to connect with the signal read-out circuit 5, and thus, the electrical load of each signal line may be kept uniform, because the arrangement pitch of unit circuits in the signal read-out circuit 5 may be same as that of the pixel pitch on the first semiconductor chip 110.

Rectangles surrounded by dashed lines within the second semiconductor chip 120 illustrated in FIGS. 4(a) and 4(b) indicate the locations of the signal read-out circuit 5 on the second surface of the second semiconductor chip 120 when the first and second semiconductor chips 110 and 120 are stacked. In the examples illustrated in FIGS. 4(a) and 4(b), the vertical scanning circuits 3 (which are not shown in FIGS. 4(a) and 4(b)) are rotated 90 degrees such that longer sides of the rectangular vertical scanning circuits 3 become, for example, parallel to longer sides of the rectangular horizontal scanning circuit 4 (which are not shown in FIGS. 4(a) and 4(b)) and the signal read-out circuit 5.

According to example embodiments, the first and second semiconductor chips may have the shapes of rectangles and may each have two parallel longer sides and two parallel shorter sides. Further, the lengths of the longer sides of the second semiconductor chip 120 may be substantially same as the lengths of the shorter sides of the first semiconductor chip 110 when the first semiconductor chip 110 is stacked on the second semiconductor chip 120 such that the longer sides of the first semiconductor chip 110 are perpendicular to the longer sides of the second semiconductor chip 120 as shown in FIG. 4(a). Further, the lengths of the longer sides of the first semiconductor chip 110 may be substantially the same or the same as the lengths of the longer sides of the second semiconductor chip 120 when the first semiconductor chip 110 is stacked on the second semiconductor chip 120 such that the longer sides of the first semiconductor chip 110 are parallel to the longer sides of the second semiconductor chip 120 as shown in FIG. 4(b). The phrase 'substantially same' as used herein with reference to the lengths of the sides of the first and second semiconductor chips 110 and 120 does not always require, for example, the length of the longer sides of the second semiconductor chip 120 to be exactly the same as that of the longer sides of the first semiconductor chip 110; but includes configurations where the length of the longer sides of the second semiconductor chip 120 on which input terminals on the signal read-out circuit 5 are located may be long enough to allow the first global wiring lines 11 to be connected electrically to the input terminals without changing a direction or layout pitch (line and space) of the lines of the first global wiring 11. With such a configuration, the distance or pitch between the lines of the first global wiring 11 may be same as that of the distance or pitch between the ADCs in the signal read-out circuit 5, and the length or the load capacitance of the first global wiring lines 11 may be reduced or, alternatively, minimized.

Figure 1D:
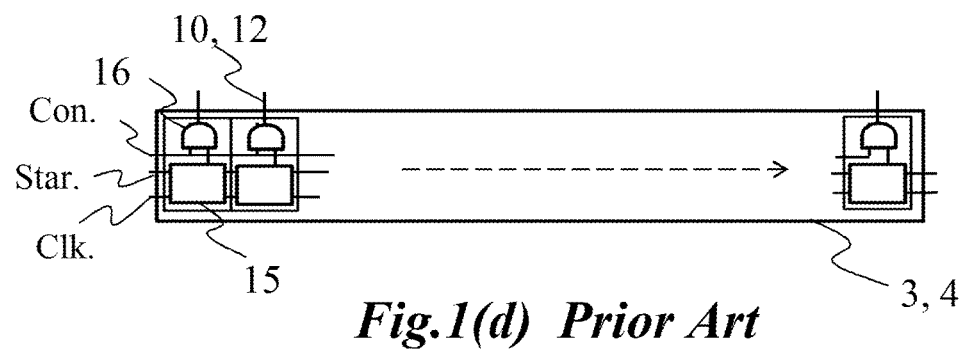
FIG. 1(d) is a diagram illustrating a plan view of a scanning circuit.
Figure 5A:
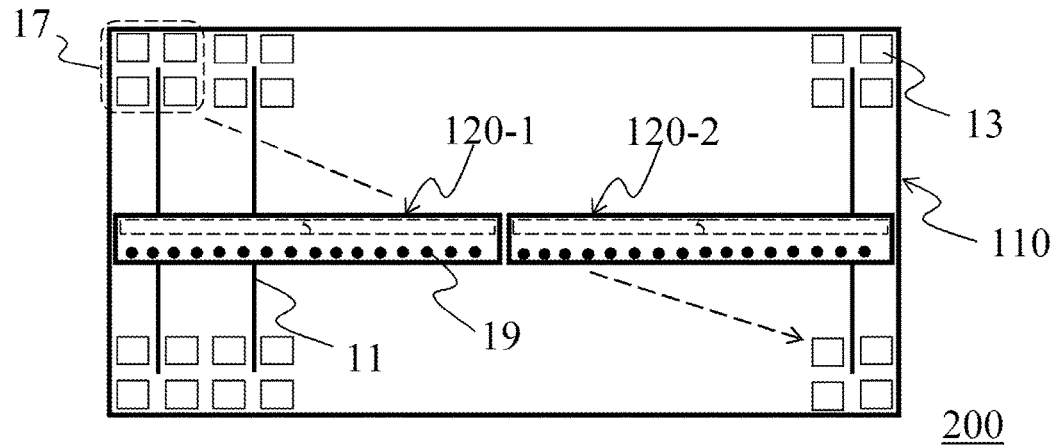
FIG. 5(a) is a diagram illustrating example locations of two second semiconductor chips relative to a first semiconductor chip according to at least one example embodiment, with respect to a plan view of a bottom side of the MOS sensor.

FIG. 5(a) is a diagram illustrating example locations of two second semiconductor chips 120 relative to the first semiconductor chip 110 according to at least one example embodiment, with respect to a plan view of a bottom side of the MOS sensor. In the example shown in FIG. 5(a), the first semiconductor chip 110 is stacked on top of two second semiconductor chips 120. According to example embodiments, the MOS sensor 200 illustrated in FIG. 5(a) may be structured such that the first semiconductor chip 110 is stacked on a series of two second semiconductor chips 120-1 and 120-2 such that the longer sides of each of the second semiconductor chips 120-1 and 120-2 are parallel to the longer sides of the first semiconductor chip 110, and the second surfaces of the second semiconductor chips are aligned with a central portion of the second surface of the first semiconductor chip 110. Between the second semiconductor chips 120-1 and 120-2, control signal lines including control (Con.), start (Sta.) and clock (Clk.) signals illustrated in FIG. 1(d), are electrically connected each other. With such a configuration, wiring resistivity along the longer sides of the second semiconductor chip 120 may be reduced even if the size of the first semiconductor chip increases. Moreover, the second semiconductor chip 120 may become even smaller, and easier to cut using dicing machine and mount on the first semiconductor chip without chipping or clacking.

Figure 5B:
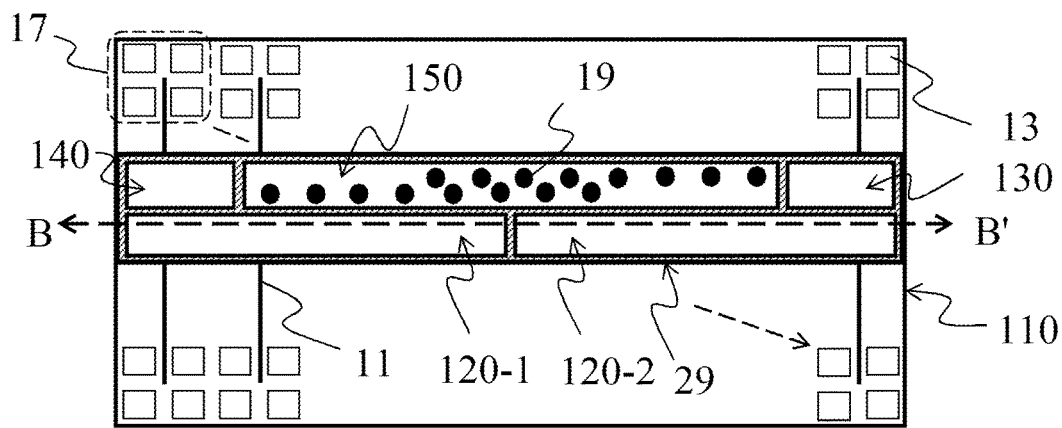
FIG. 5(b) is a diagram illustrating example locations of two second semiconductor chips on an interposer relative to a first semiconductor chip according to at least one example embodiment, with respect to a plan view of a bottom side of the MOS sensor.

FIG. 5(b) is a diagram illustrating example locations of two second semiconductor chips 120 on an interposer chip 29 relative to a first semiconductor chip 110 according to at least one example embodiment, with respect to a plan view of a bottom side of the MOS sensor. As is illustrated in FIG. 5(b), the first semiconductor chip 110 may be stacked on the interposer chip 29, and the interposer chip 29 may be stacked second semiconductor chips 120. In the example illustrated in FIG. 5(b), the interposer chip 29 is stacked on the second semiconductor chips 120-1, 120-2 and other chips 130, 140 and 150. The semiconductor chip 130 includes, for example, timing pulse and control signal generation (TG) circuits. The semiconductor chip 140 may include, for example, a digital signal processing (DSP) and a data compression circuit, for example. The semiconductor chip 150 may include, for example, an interface circuit. According to example embodiments, the interposer chip 29 may be shaped as a rectangle where the size of a footprint of the interposer chip 29 is smaller than that of the first semiconductor chip 110 with respect to, for example, a plan view of the MOS sensor 100. For example, according to example embodiments, the MOS sensor 100 may be configured such that none of the boundaries of the footprint of the interposer chip 29 fall outside the boundaries of the footprint of the first semiconductor chip 110. For example, according to example embodiments, the footprint of the first semiconductor chip 110 may overlap the footprint of the interposer chip 29 entirely, with respect to a plan view of the MOS sensor 100.

Figure 5C:
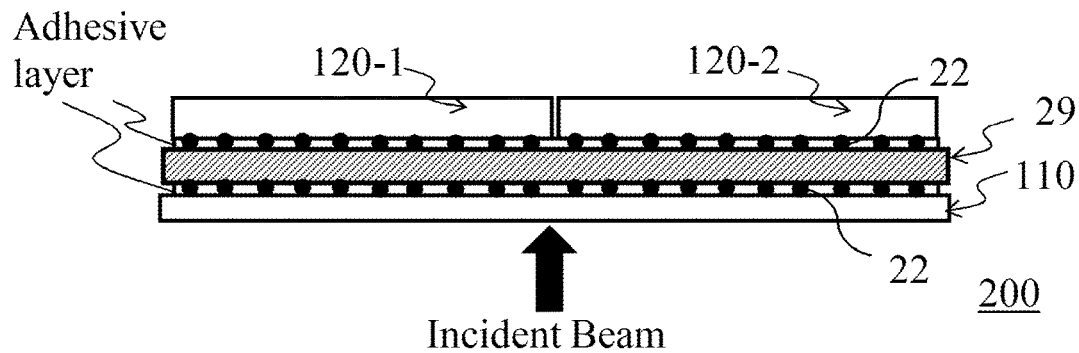
FIG. 5(c) is a diagram illustrating a cross sectional view taken along line B-B' of the MOS sensor illustrated in FIG. 5(b) according to at least one example embodiment.

FIG. 5(*c*) is a diagram illustrating a cross sectional view taken along line B-B' of the MOS sensor 200 illustrated in FIG. 5(*b*) according to at least one example embodiment. According to example embodiments, micro-pads (which are not shown in FIG. 5(*c*)) may be formed on both surfaces of the interposer chip 29 (i.e., the surface of the interposer chip 29 facing the second surface of the first semiconductor chip 110 and the surface of the interposer chip 20 facing the second surface of the second semiconductor chip 120). More than two wiring layers may be formed in the interposer chip 29 and electrically connected with the micro-pads. In the example illustrated in FIG. 5(*c*), micro-pads on semiconductor chips including, for example, the second semiconductor chips 120-1 and 120-2, and the first semiconductor chip 110, are electrically connected with the micro-pads on the interposer chip 29 through micro-bumps 22 located between pairs of opposing micro-pads belonging, respectively, to pairs of stacked semiconductor chips. With such a configuration, it may not be necessary for the second semiconductor chips 120-1 and 120-2 to integrate peripheral circuits such as timing TG and DSP circuits on the long and thin shaped chips. It becomes easy to optimize instead, the performance and specifications of each of the second semiconductor chips 120-1 and 120-2 may be configured to desired or, alternatively, optimized levels depending on the system to which the second semiconductor chips 120-1 and 120-2 are applied including, for example, a medical X-ray imaging system. In addition, image data; which may be transferred from the signal read-out circuit, may be compressed by another semiconductor chip on the interposer 29. As a result, large volume data may be read out with a lower clock frequency or lower power consumption, for example.

Figure 6A:
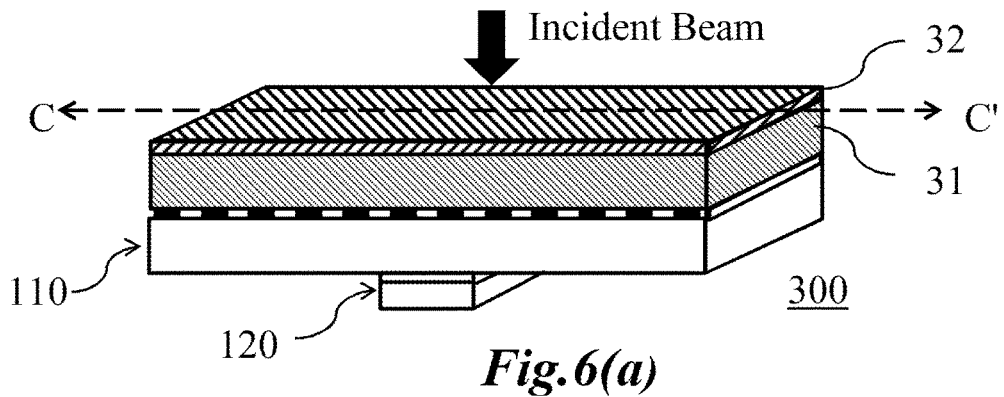
FIG. 6(a) is a diagram illustrating an example configuration of a MOS sensor on which a photo-conductive material or layer is deposited according to at least one example embodiment, with respect to a perspective view of the MOS sensor.
Figure 6B:
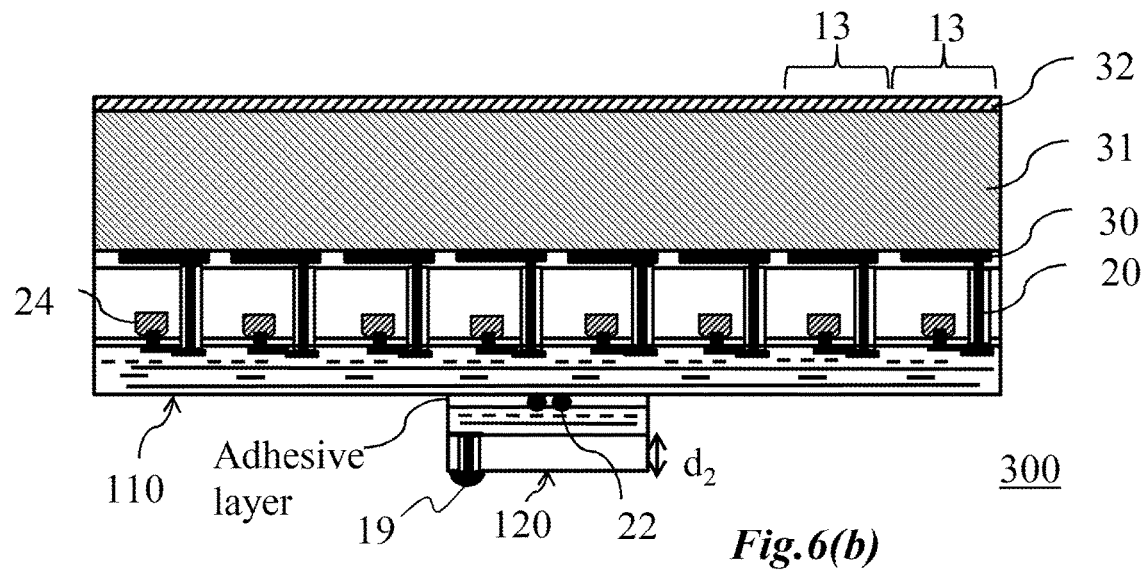
FIG. 6(b) is a diagram illustrating a cross sectional view taken along line C-C' of the MOS sensor illustrated in FIG. 6(a) according to at least one example embodiment.
Figure 6C:
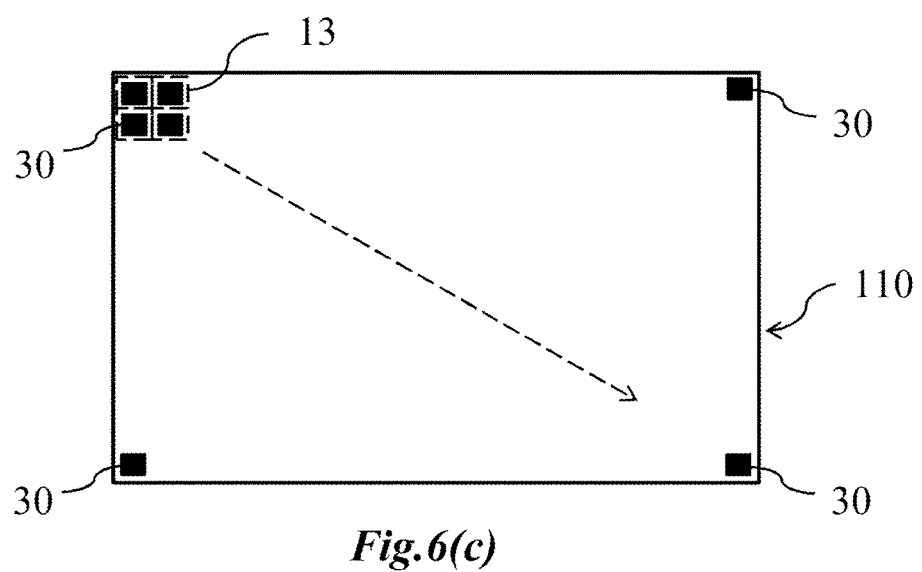
FIG. 6(c) is a diagram illustrating an example of an array of pixel electrodes on a first semiconductor chip according to at least one example embodiment, with respect to plan view of the array of pixel electrodes.

FIG. 6(*a*) is a diagram illustrating an example configuration of a MOS sensor 300 on which a photoconductive layer material or layer is deposited according to at least one example embodiment, with respect to a perspective view of the MOS sensor. FIG. 6(*b*) is a diagram illustrating a cross sectional view taken along line C-C' of the MOS sensor 300 according to at least one example embodiment. FIG. 6(*c*) is a diagram illustrating an example of an array of pixel electrodes 30 on the first semiconductor chip 110 according to at least one example embodiment, with respect to a plan view of the array of pixel electrodes 30.

As is illustrated in FIGS. 6(*a*) and 6(*b*), the MOS sensor 300 includes a first semiconductor chip 110 stacked on a second semiconductor chip 120. Photo-electric conversion may be performed in a photo-conductive layer 31, which is formed above the first surface of the first semiconductor chip 110 as illustrated in FIGS. 6(*a*) and 6(*b*). In the examples illustrated in illustrated in FIGS. 6(*a*) and 6(*b*), the photo-conductive layer 31 is sandwiched between a counter electrode layer 32 and an array of pixel electrodes 30, which are formed on the first surface of the first semiconductor chip 110. In the example illustrated in FIG. 6(*b*), each pixel electrode 30 is electrically connected with a drain terminal 24 in each pixel 13 by a TSV 20. With such a configuration, a large photo-conductive area may be formed with relative ease by physical or chemical vapor deposition of a photo-conductive material or layer.

The photo-conductive layer 31 may be composed of, for example, an amorphous semiconductor, a micro-crystalline semiconductor, an organic semiconductor, or a compound including one or more of these materials. For example, the composition of the photo-conductive layer 31 may selected depending on a wavelength or energy of an incident beam the MOS sensor is configured to capture. A-Se, tellurium cadmium (CdTe), gallium arsenide (GaAs), silver iodide (AgI) may be used, for example, as an X-ray direct conversion layer. A chemical or physical vapor deposition (CVD or PVD) method may be used to form a relatively large area photo-conductive layer 31 over the first semiconductor chip 110. With such a configuration, not only visible light image but also X-ray image may be captured by the MOS 300 with a higher sensitivity.

As shown in FIG. 6(*b*), a thickness ($d_2$) of the silicon substrate of the second semiconductor chip 120 may have a range 50 nanometers to 1 micron meter. According to example embodiments, this configuration may reduce the generation of undesirable charges, which may result from X-rays penetrating through the first semiconductor chip 110 and may cause radiation damage in the second semiconductor chip 120. Conventionally, a lead or tungsten sheet has been placed on the peripheral circuits around the image sensing area in order to attenuate or screen incident X-ray. However, it may be difficult or, alternatively, impossible to use these metal sheets for the stacked type image sensor, because the metal sheets may prevent electrical communication between the stacked chips of the stacked type image sensor. Regarding the second semiconductor chip 120, according to example embodiments, the silicon substrate may be thinned by chemical mechanical polishing (CMP), or a SOI (silicon on insulator) substrate may be used instead.

Figure 7A:
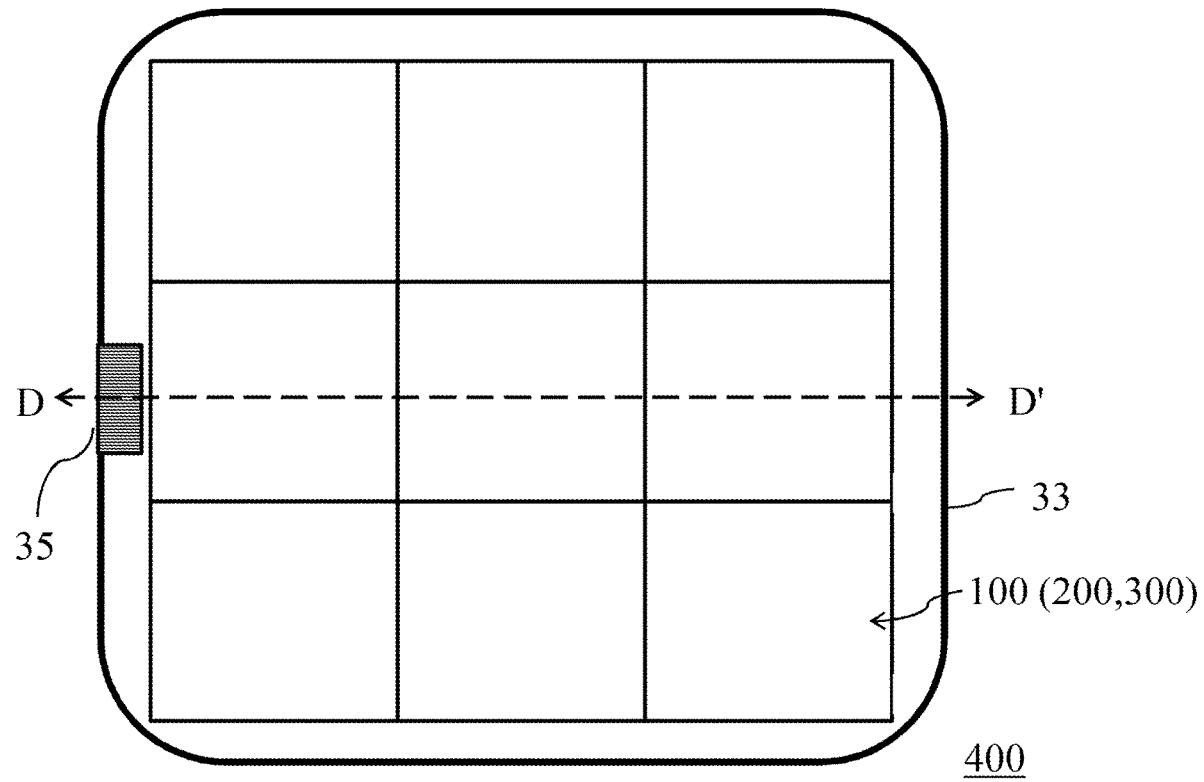
FIG. 7(a) is a diagram illustrating an example of a multifaceted flat panel detector (FPD) according to at least one example embodiment, with respect to a plan view of the FPD.

FIG. 7(*a*) is a diagram illustrating an example of a multifaceted flat panel detector (FPD) 400 including tiled MOS sensors 100. FIG. 7(*b*) is a diagram illustrating a cross sectional view of the FPD 400 taken along the line D-D' in FIG. 7(*a*), according to example embodiments. Though, for the purpose of simplicity, the FPD 400 will be described with respect to an example where the FPD 400 includes plural instances of the MOS sensor 100, the FPD 400 may also use either or both of the MOS sensors 200 or 300 with, or in place of, the MOS sensors 100. Accordingly, where sensors having the structure of the MOS 100 are discussed herein as being included in an FPD, it will be understood that any or all of the sensors having the structure of the MOS sensor 100 may be replaced with sensors having the structure of the MOS sensor 200 or the MOS sensor 300.

Figure 7B:
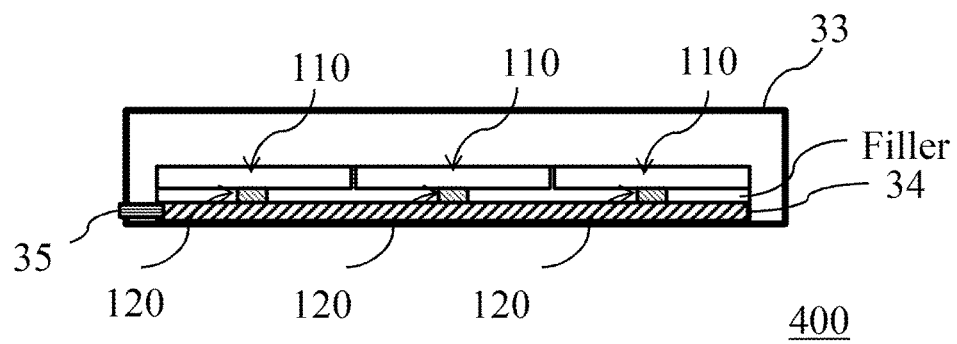
FIG. 7(b) is a diagram illustrating a cross sectional view taken along line D-D' of the multifaceted FPD illustrated in FIG. 7(a) according to at least one example embodiment FIG. 8 (a) is a diagram illustrating a cross sectional view taken along line D-D' of the multifaceted FPD illustrated in FIG. 7(a) according to at least one example embodiment, where a photoconductive material or layer is deposited on first surfaces of first semiconductor chips of the multifaceted FPD.

In the example shown in FIG. 7(*a*), nine MOS sensors 100 are assembled in the case or cassette 33 in a 3×3 arrangement, and the case or cassette 33 is equipped with a socket 35. Though, 9 MOS sensors are included in the example FPD 400 illustrated in FIG. 7(*a*), according to example embodiments the FPD 400 may include any number of sensors arranged, for example, in a 'n' by 'm' array where 'n' is a positive integer representing a number of rows in the array, 'm' is a positive integer representing a number of columns in the array, at least one of 'n' and 'm' is greater than 1, and each of the sensors included in the array has the structure of the MOS sensor 100. In the example illustrated in FIG. 7(*b*), the MOS sensors 100 are stacked on a printed circuit board 34. According to example embodiments, the MOS sensors 100 may be fixed to the printed circuit board 34 by an adhesive layer between the MOS sensors 100 and the printed circuit board 34. Further spaces between the first semiconductor chips 110 of the MOS sensors 100 included in the FPD 400 and spaces in between the second semiconductor chips 120 of the MOS sensors 100 included in the FPD 400 may be filled up with filler or filling such as an epoxy resin or a poly amide, as is illustrated in FIG. 7(b). With such a configuration, the image sensing area of the FPD 400 may be enlarged, and the FPD 400 may be able to employ a higher data transfer rate through the use of parallel data reading with respect to the individual MOS sensors included in the FPD 400, without increasing the clock frequency. Consequently, with the FPD 400 according to example embodiments, real time imaging for moving organs such as beating heart under the X-ray exposure may be realized with one or both of lower clock frequency and lower power consumption in comparison with conventional X-ray imaging systems.

Figure 8A:
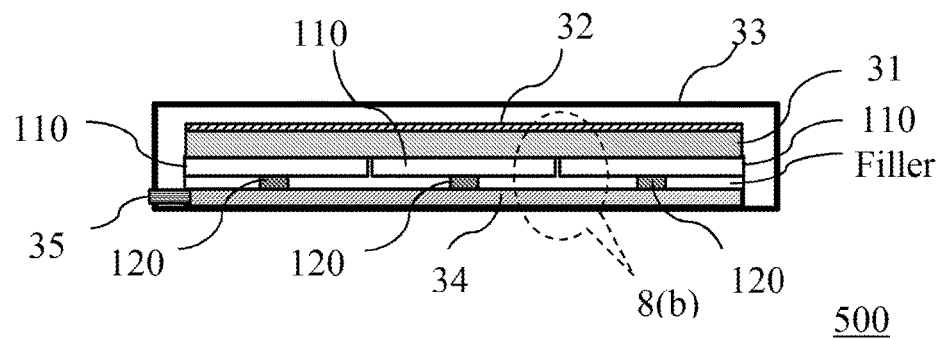
FIG. 8(b) is a diagram illustrating an enlarged portion of the cross sectional view illustrated in FIG. 8(a), as indicated by the dashed lines around a portion of the chip boundary shown in FIG. 8(a), according to at least one example embodiment.

FIG. 8(a) is a diagram illustrating a cross sectional view of an FPD 500. The cross section al view of the FPD 500 represents an example of a cross sectional view taken along line D-D' of the multifaceted FPD 400 illustrated in FIG. 7(a), with respect to an arrangement where a photoconductive material or layer 31 and a counter electrode 32 are applied to coat first surfaces of first semiconductor chips 100 of the multifaceted FPD 400. For example, in the example illustrated in FIG. 8(a), the tiled MOS sensors of the FPD 500, each including a first semiconductor chip 110 stacked on a second semiconductor chip 120, are covered by the photo-conductive material or layer 31 and a counter electrode 32, according to example embodiments.

Figure 8B:
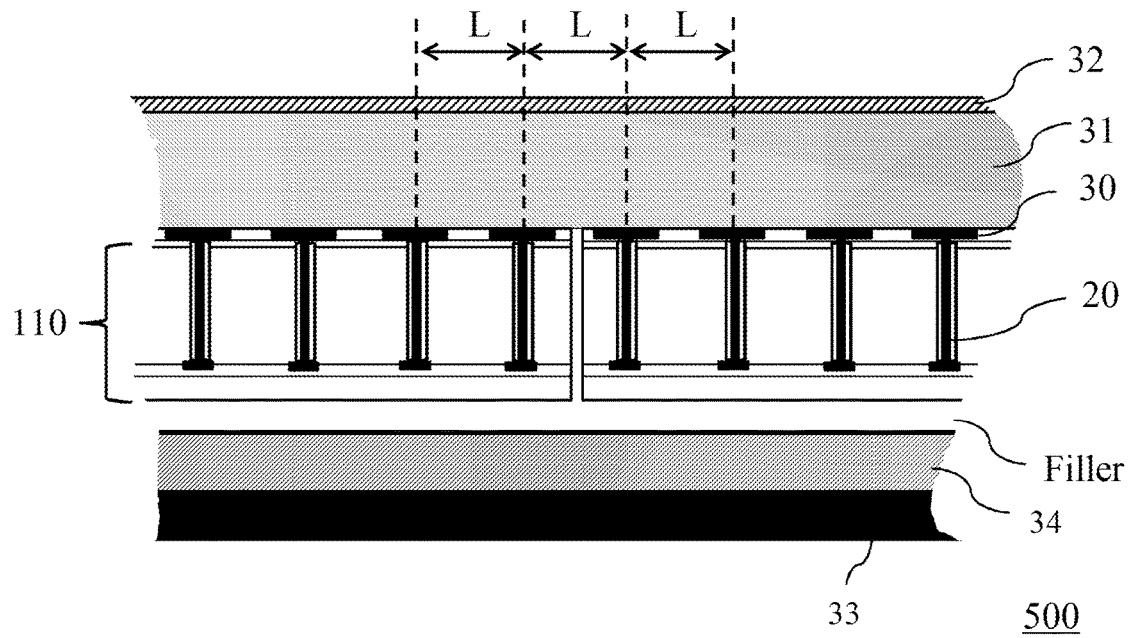

FIG. 8(b) is a diagram illustrating an enlarged portion of the cross sectional view of the FPD 500 illustrated in FIG. 8(a), as indicated by the dashed lines labeled '8(b)' around a portion of the chip boundary shown in FIG. 8(a), according to at least one example embodiment. In the examples illustrated in FIGS. 8(a) and 8(b), pixel electrodes 30 are formed on the first semiconductor chips 110. Further spaces in between the first semiconductor chips 110 and space in between the second semiconductor chips 120 may be filled up with filler or filling such as an epoxy resin or a poly amid, as illustrated in FIGS. 8(a) and 8(b). With such a configuration, sensor characteristics including sensitivities of the tiled MOS sensors included in the FPD 500 may become uniform because the single photo-conductive layer 31 is coated over the multiple first semiconductor chips 110. In addition, a reduction of particles and pixel defects may be experienced during manufacturing operations of the FPD 500 according to example embodiments. As a result, the process of manufacturing the FPD 500 may be simplified and a production yield associated with the manufacturing process may be improved compared to a conventional manufacturing process in which a process of tiling MOS sensors is performed after the photo-conductive layer 31 and the counter electrode 32 are coated on chips of each of the MOS sensors.

According to example embodiments, it may be desirable to form the edges of the first semiconductor chips 110 corresponding to each of the MOS sensors 100 included in FPD 500, or the FPD 400, such that a pitch (e.g., the center pitch L illustrated in FIG. 8(b)) between pixel electrodes 30 on the edges of two adjacent first semiconductor chips 110 matches a pitch (e.g., the left or right pitch L illustrated in FIG. 8(b)) between adjacent pixel electrodes on a single one of the first semiconductor chips 110, as is illustrated by the pitches L illustrated in FIG. 8(b). With such a configuration, dead space or missing pixels between the multiple MOS sensors 100 included in the FPD 500 or 400 may be reduced or, alternatively, minimized or eliminated. Further, the arrangement discussed above with reference to FIG. 8(b) may allow for pixel sampling points to be equally spaced over an entire image sensing area, including each of the image sensing areas 2 of the multiple MOS sensors 100, in the FPD 500 or 400. If, as in some conventional image sensors, the second semiconductor chips 120 of the tiled array of MOS sensors 100 included in the FPD 500 or 400 were larger than the first semiconductor chips 110 of the tiled MOS sensors 100, the second semiconductor chips 120 would form regions of dead space and missing pixels between the tiled MOS sensors 100. Accordingly, as is discussed above, according to example embodiments, the size of the second semiconductor chips 120 are smaller than the sizes of the first semiconductor chips 110, thus facilitating the process of reducing or, alternatively, minimizing or eliminating missing pixels and dead space in between tiled MOS sensors 100 of the FPD 400 or 500. Thus the FPDs 400 and 500 according to example embodiments may include m×n arrays of MOS sensors 100 where the values 'm' and 'n' may each be any positive integer. For example, one or both the values 'm' and 'n' may be greater than 2. Thus, because, according to example embodiments, a footprint of the first semiconductor chip 110 may overlap the smaller footprint of the second semiconductor chip 120 entirely with respect to a plan perspective of the MOS sensor 100, the FPDs 400 and 500 may include for example, 2×3, 2×4, or 3×3 arrays of the MOS sensors 100 while still maintaining little or no dead space in between the MOS sensors 100, and while still maintaining uniform pitch between pixel electrodes 30 across an entirety of the combined image sensing areas 2 of the MOS sensors 100 included in the FPD 400 or 500.

Figure 9:
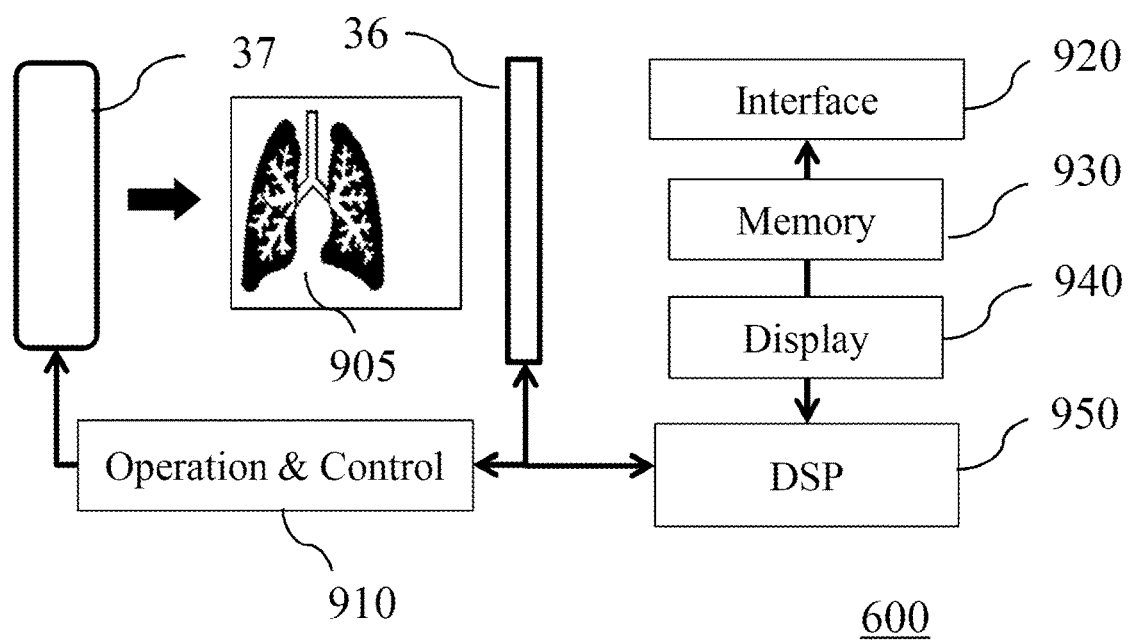
FIG. 9 is a block diagram illustrating an example of a medical X-ray imaging system that includes a MOS sensor and/or a FPD according to at least one example embodiment.

FIG. 9 illustrates an example of a medical X-ray imaging system 600 employing a FPD according to example embodiments including, for example, the FPD 400 or the FPD 500. In the example illustrated in FIG. 9, the medical X-ray imaging system 600 includes a FPD unit 36, an X-ray source 37, an operation panel 910, a DSP unit 950, a display 940, a memory 930, and an interface unit 920. An X-ray image, formed by X-rays passing through a subject 905 may be captured by the FPD 36, and the FPD 36 may be controlled by the operation panel 910 synchronizing with the exposure of X-ray source 37. Image data transferred from the FPD 36 may be processed by the DSP 950. The DSP 950 may perform operations including data compression, for example. The image data processed by the DSP 950 may be displayed on the display 940, stored in the memory 930, and/or accessed by a communications network, including for example a local network or the internet, through the interface unit 920.

According to example embodiments, the medical X-ray imaging system 600 may have first and second operation modes. The first operation mode may be a motion picture mode which may enable the X-ray imaging system 600 to capture a moving object like a blood vessel around a beating heart. Further, by adding the electrical signals generated based on X-rays incident on four adjacent pixels using, for example, the pixel circuit 17 shown in FIG. 1(b), the sensitivity of the X-ray imaging system 600 may become four times higher. Consequently, according to example embodiments, the X-ray imaging system 600 may obtain moving X-ray images or X-ray video of a patient, while exposing the patient to, for example, 75% less X-ray radiation in comparison to the radiation exposure associated with capturing still X-ray images.

According to example embodiments, the second operation mode of the X-ray imaging system 600 may be a still picture mode. In the second operation mode, the X-ray imaging system 600 may capture a full resolution still image of a subject, which may contribute to an accurate medical diagnosis associated with the subject of the capture still X-ray image.

Figure 10:
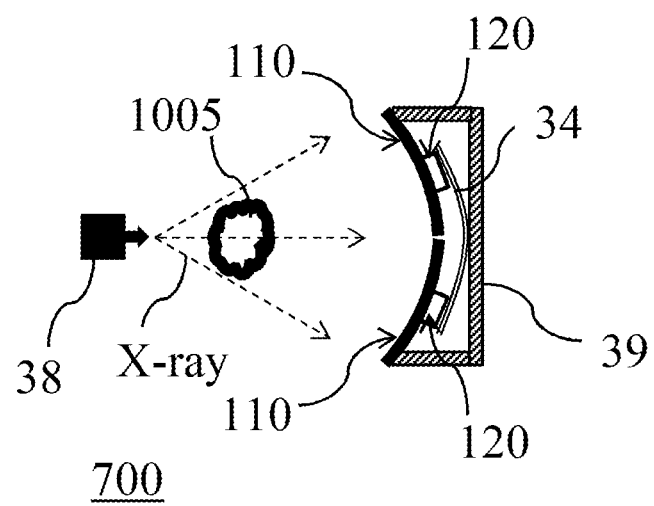
FIG. 10 is a diagram illustrating an example configuration of an X-ray imaging system that includes a MOS sensor and/or FPD having a curved surface according to at least one example embodiment.

FIG. 10 is a diagram illustrating an example configuration of an X-ray imaging system 700 that includes a MOS sensor 100 and/or FPD having a curved surface according to at least one example embodiment. In the example illustrated in FIG. 10, a detector unit 39 includes an FPD formed by a PCB 34 upon which two MOS sensors 100 are stacked. Each of the MOS sensors 100 included in the FPD of the detector unit 39 include a first semiconductor chip 110 stacked on a second semiconductor chip 120, as is illustrated in FIG. 10. Further, as is illustrated in FIG. 10, the FPD of the detector unit 39 has a curved surface due to the curved surfaces of the first semiconductor chips 110 included in the FPD. According to example embodiments, the first semiconductor chips 110 and the PCB 34 are curved cylindrically such that centers of curvature for the first semiconductor chips 110 of the detector unit 39 are located on the same side of the first semiconductor chips 110 as the subject 1005 and an X-ray source 38, and such that X-rays generated by the X-ray source 38 are incident on the image sensing areas 2 of the first semiconductor chips 110 at right angles. With such a configuration, an isotropic and uniform image capturing may be realized with respect to incoming X-rays that would have had different incident angles if received by an image sensors having flat (i.e., non-curved) image sensing areas 2. Consequently, a post image processing algorithm corresponding to X-ray images formed based on such X-rays may be simplified. If, as in some conventional image sensors, the second semiconductor chip 120 was larger than the first semiconductor chip 110, forming the first semiconductor chip 110 to include the curved image sensing area 2 discussed above may be very difficult or, alternatively, not possible. Accordingly, as is discussed above, according to example embodiments, the size of the second semiconductor chip 120 is smaller than the size of the first semiconductor chip, thus facilitating the process of forming to first semiconductor chip 110 to include the curved image sensing area 2.

According to example embodiments, The X-ray source 38 may be a micro-focused X-ray generator forming, for example, a cone beam type X-ray. The X-ray source 38 and the detector unit 39 may be mounted on a c-shape arm (which is not shown in this figure) such that a center axis of a partial cylinder formed by the curved surface of the FPD of the detector unit 39 may be aligned to be parallel to a center axis of a subject including, for example, a human body, or aligned to be parallel to a direction of a computer tomography (CT) scanning. For example, by rotating the c-shape arm 180 or 360 degrees, for example, the X-ray image system 700 may obtain three dimensional (3D) images from inside the human body. Further, by moving or scanning the c-shape arm along the center axis of the human body or that of the partial cylinder formed by the curved surface of the FPD of the detector unit 39, an entire 3D image of the human body or patient may be captured by the X-ray imaging system 700 within period of time that may be relatively short and may be limited, thereby reducing an amount X-ray radiation to which a patient is exposed. According to example embodiments, the X-ray imaging system 700, which may be implemented as a cone-beam X-ray type CT scanner in the manner discussed above, may employ one or more of the MOS sensor 100, 200 and 300 and the FPD 400 and 500 described above. According to example embodiments, the cone-beam X-ray type CT scanner 700 may capture high resolution, high image quality 3D X-ray image using a lower X-ray radiation dose and a shorter examination time. As a result, a disease or other condition harmful to the health of a patient may be discovered accurately in the early stages of the condition thereby reducing medical expenses.

The example embodiments of MOS sensors and FPDs are described above in the context of medical image systems, the MOS sensors and FPDs according to example embodiments re not limited to medical applications. For example, according to example embodiments, a scintillator may be layered above the pn junction, or on the a-Si layer an MOS sensor described herein. Further, additional example applications for the an MOS sensor or FPD disclosed herein include, but are not limited to, X-ray phase shift imaging using, for example, a micro-focused X-ray source, various industrial X-ray imaging systems, X-ray astronomy, and high energy physics applications.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed:

1. An image sensor comprising:
a first semiconductor chip having a first surface and a second surface;
a second semiconductor chip having a first surface and a second surface; and
a first adhesive layer between the second surface of the first semiconductor chip and the second surface of the second semiconductor chip,
the first semiconductor chip being stacked on the second semiconductor chip via the first adhesive layer such that the second surface of the first semiconductor chip faces the second surface of the second semiconductor chip, and a footprint of the first semiconductor chip is larger than a footprint of the second semiconductor chip with respect to a plan view of the image sensor,
the first semiconductor chip including an image sensing area, the image sensing area including an array of unit pixels configured to capture light corresponding to an image and to generate image signals based on the captured light, the second surface of the first semiconductor chip including first contact pads connected to the unit pixels,
the second semiconductor chip including first peripheral circuits configured to control the array of unit pixels and receive the generated image signals, the first peripheral circuits including a vertical scanning circuit, a horizontal scanning circuit, and a signal read-out circuit, the second surface of the second semiconductor chip including second contact pads connected to the first peripheral circuits, and
the first contact pads being electrically connected through the first adhesive layer to the second contact pads,
wherein,
the first peripheral circuits are located on a portion of the second semiconductor chip that falls inside a footprint of the image sensing area of the first semiconductor chip, with respect to the plan view of the image sensor, the horizontal scanning circuit and the vertical scanning circuit are each rectangular, and not square, in shape such that the horizontal scanning circuit and the vertical scanning circuit each have two parallel longer sides and two parallel shorter sides, and the first peripheral circuits are arranged on the second surface of the second semiconductor chip such that the longer sides of the vertical scanning circuit are parallel to the longer sides of the horizontal scanning circuit.

2. The image sensor of claim 1, wherein the first semiconductor chip includes a silicon substrate having a thickness in a range of 0.5 to 20 microns.

3. The image sensor of claim 1 wherein,
the first semiconductor chip includes first circuits, the first circuits being all circuits in the first semiconductor chip that include transistors, and
either,
all the transistors included in the first circuits are NMOS type transistors and not PMOS type transistors, or
all the transistors included in the first circuits are PMOS type transistors and not NMOS type transistors.

4. The image sensor of claim 1, wherein the first semiconductor chip includes a wiring layer and the wiring layer includes first wires, second wires and third wires,
the first wires connecting pixels from among the array of unit pixels to the signal read-out circuit of the second semiconductor chip, and being configured to transfer signals read from the array of unit pixels to the signal read-out circuit,
the second wires being connected to pixels from among the array of unit pixels, and being configured to transfer control signals received from the third wires to the array of unit pixels, and
the third wires connecting the vertical scanning circuit to the second wires such that the third wires are parallel to the first wires.

5. The image sensor of claim 1 wherein,
the first semiconductor chip and the second semiconductor chip are each rectangular, and not square, in shape such that the first semiconductor chip and the second semiconductor chip each have two parallel longer sides and two parallel shorter sides, and
either,
lengths of the longer sides of the second semiconductor chip are substantially the same as lengths of the shorter sides of the first semiconductor chip, and the first semiconductor chip is stacked on the second semiconductor chip such that the longer sides of the first semiconductor chip are perpendicular to the longer sides of the second semiconductor chip, or
lengths of the longer sides of the first semiconductor chip are substantially the same as lengths of the longer sides of the second semiconductor chip, and the first semiconductor chip is stacked on the second semiconductor chip such that the longer sides of the first semiconductor chip are parallel to the longer sides of the second semiconductor chip.

6. The image sensor of claim 1 wherein,
the signal read-out circuit is rectangular, and not square, in shape such that the signal read-out circuit has two parallel longer sides and two parallel shorter sides,
the first semiconductor chip includes a wiring layer and the wiring layer includes first wires, and the first wires connect pixels from among the array of unit pixels to the signal read-out circuit of the second semiconductor chip,
the first wires being directly connected to micro-pads that are electrically connected to the signal read-out circuit such that an angle formed at an intersection of a line having a same direction as the first wires and a line having the same direction as the longer sides of the signal read-out circuit is substantially a right angle with respect to the plan view of the image sensor,
the first wires being configured to transfer signals read from the array of unit pixels to the signal read-out circuit.

7. The image sensor of claim 1, wherein the signal read-out circuit is located on a portion of the second semiconductor chip that falls in the middle of the footprint of the image sensing area of the first semiconductor chip, with respect to the plan view of the image sensor.

8. The image sensor of claim 1, further comprising:
a third semiconductor chip including first and second surfaces,
wherein the first semiconductor chip, the second semiconductor chip, and the third semiconductor chip are each rectangular, and not square, in shape such that each has two parallel longer sides and two parallel shorter sides,
wherein the third semiconductor chip is arranged beside the second semiconductor chip in series with the second semiconductor chip, and
wherein the first semiconductor chip is stacked on both the second semiconductor chip and the third semiconductor chip via the first adhesive layer such that,
the longer sides of the first semiconductor chip are parallel to the longer sides of the second semiconductor chip and the longer sides of the third semiconductor chip, and
a footprint of the first semiconductor chip is larger than a combined footprint of the second semiconductor chip and the third semiconductor chip with respect to the plan view of the image sensor.

9. The image sensor of claim 8, further comprising:
an interposer chip having first and second surfaces; and
a second adhesive layer,
wherein the second surfaces of the second and third semiconductor chips are attached to the second surface of the interposer chip by the second adhesive layer such that the interposer chip is stacked on the second and third semiconductor chips, and
wherein the first surface of the interposer chip is attached to the second surface of the first semiconductor chip such that the first semiconductor chip is stacked on the interposer chip.

10. The image sensor of claim 9, further comprising:
one or more additional semiconductor chips, the one or more additional semiconductor chips including a digital signal processing circuit and a data compression circuit,
wherein the one or more additional semiconductor chips each have first and second surfaces, and
wherein the second surfaces of the one or more additional semiconductor chips are attached to the second surface of the interposer chip by the second adhesive layer such that the interposer chip is stacked on the second and third semiconductor chips and the one or more additional semiconductor chips.

11. The image sensor of claim 1, further comprising:
a photo-conductive layer above the first semiconductor chip,
wherein the first semiconductor chip includes an array of pixel electrodes corresponding to the array of unit pixels, and
wherein the a photo-conductive layer coats the array of pixel electrodes.

12. The image sensor of claim 11,
wherein the photo-conductive layer is a direct conversion type photo-conductive material.

13. The image sensor of claim 1, wherein the second semiconductor chip includes a silicon substrate having a thickness in a range of 50 nanometers to 1 micron.

14. A flat panel detector (FPD) comprising:
an array of first sensors; and
a case holding the array of first sensors,
wherein each one of the first sensors is the image sensor of claim 1.

15. The FPD of claim 14 further comprising:
a photo-conductive layer,
wherein, for each of the first sensors,
the first sensor includes an array of pixel electrodes corresponding to the array of unit pixels, and
the array of pixel electrodes are spaced uniformly such that a first pitch between each of the pixel electrodes in the array of pixel electrodes is uniform, and
wherein edges of the first sensors are sized such that, for each pair of adjacent first sensors in the array of first sensors, a pitch between first pixel electrodes on a first edge and second pixel electrodes on a second edge is the first pitch, the first and second edges being adjacent edges of the first and second ones of the pair of adjacent first sensors.

16. An X-ray imaging system comprising:
an X-ray source configured to emit X-ray radiation through a subject; and
the FPD of claim 14 configured to receive the X-ray radiation and generate image signals corresponding to the subject based on the received X-ray radiation.

17. A flat panel detector (FPD) comprising:
an array of first sensors; and
a case holding the array of first sensors,
wherein each one of the first sensors is the image sensor of claim 2, and
wherein the image sensing areas of the first sensors are curved such that the image sensing areas of the first sensors, together, form a semi cylindrical shape.

18. An X-ray imaging system comprising:
an X-ray source configured to emit X-ray radiation through a subject; and
the FPD of claim 17 configured to receive the X-ray radiation and generate image signals corresponding to the subject based on the received X-ray radiation.

* * * * *